US010303852B2

(12) United States Patent
Peterson et al.

(10) Patent No.: US 10,303,852 B2
(45) Date of Patent: May 28, 2019

(54) DECISION SUPPORT TOOL FOR USE WITH A MEDICAL MONITOR-DEFIBRILLATOR

(71) Applicants:Ken Peterson, Bellevue, WA (US); Mitchell A Smith, Sammamish, WA (US); Denny Craig Edwards, Fall City, WA (US); Nathaniel Paul Barcelos, Clemmons, NC (US); James Wootten, Kirkland, WA (US); Clayton Young, Redmond, WA (US); Randy L. Merry, Woodinville, WA (US); Dana S Lewis, Woodinville, WA (US); John C Daynes, Redmond, WA (US); Paul R Juhasz, Houston, TX (US); David Okey, Rockford, IL (US); Steven Witters, LaGrange, KY (US); Ira M Turner, Wallingford, CT (US)

(72) Inventors: Ken Peterson, Bellevue, WA (US); Mitchell A Smith, Sammamish, WA (US); Denny Craig Edwards, Fall City, WA (US); Nathaniel Paul Barcelos, Clemmons, NC (US); James Wootten, Kirkland, WA (US); Clayton Young, Redmond, WA (US); Randy L. Merry, Woodinville, WA (US); Dana S Lewis, Woodinville, WA (US); John C Daynes, Redmond, WA (US); Paul R Juhasz, Houston, TX (US); David Okey, Rockford, IL (US); Steven Witters, LaGrange, KY (US); Ira M Turner, Wallingford, CT (US)

(73) Assignee: PHYSIO-CONTROL, INC., Redmond, WA (US)

( * ) Notice: Subject to any disclaimer, the term of this patent is extended or adjusted under 35 U.S.C. 154(b) by 222 days.

(21) Appl. No.: 13/836,769

(22) Filed: Mar. 15, 2013

(65) Prior Publication Data
US 2014/0272860 A1    Sep. 18, 2014
US 2016/0180037 A9    Jun. 23, 2016

Related U.S. Application Data

(60) Provisional application No. 61/667,142, filed on Jul. 2, 2012.

(51) Int. Cl.
*G06F 17/00* (2006.01)
*G06N 5/02* (2006.01)
(Continued)

(52) U.S. Cl.
CPC ............ *G06F 19/345* (2013.01); *A61B 5/002* (2013.01); *A61B 5/02055* (2013.01);
(Continued)

(58) Field of Classification Search
None
See application file for complete search history.

(56) References Cited

U.S. PATENT DOCUMENTS 3,724,455 A    4/1973   Unger
3,865,101 A    2/1975   Saper
(Continued)

FOREIGN PATENT DOCUMENTS

EP    0801959 A2    10/1997
EP    0923961 A1    6/1999
(Continued)

OTHER PUBLICATIONS

Int'l Search Report and Written Opinion, PCT/US2012/071436, mailed Apr. 10, 2013, 13 pages.
(Continued)

*Primary Examiner* — Li-Wu Chang
(74) *Attorney, Agent, or Firm* — Lane Powell PC

(57) ABSTRACT

Work flows are modeled as a graph of interdependent tasks to be performed. The tasks to be performed are set by a task file module configured to enable interactions between tasks and including modules for event viewing, protocol assis-
(Continued)

tance, smart messaging, smart indices, reference material lookup. A decision support manager module is configured to construct data and model profiles for storage in a data and model profile bank, events for storage in a decision support events bank, and protocols for storage in a decision support protocol bank. Configuration files are provided to specify a configuration for execution of one of the tasks. Data entered through a user interface or from a network via a wireless or wired communication module may define task files in the task files module, configuration files in the configuration files module, as well as data, events, and protocols to be used for a defibrillation procedure. A decision support manager module is configured to construct a dependency graph of tasks as specified in at least one of the configuration files and to execute the dependency graph.

52 Claims, 19 Drawing Sheets

(51) Int. Cl.
G06F 19/00 (2018.01)
A61B 5/00 (2006.01)
A61B 5/0205 (2006.01)
A61B 5/0402 (2006.01)
A61N 1/39 (2006.01)
A61B 5/021 (2006.01)
A61B 5/083 (2006.01)
A61B 5/1455 (2006.01)

(52) U.S. Cl.
CPC .......... *A61B 5/0402* (2013.01); *A61B 5/4836* (2013.01); *A61N 1/3993* (2013.01); *A61B 5/021* (2013.01); *A61B 5/0836* (2013.01); *A61B 5/14551* (2013.01); *A61B 5/7282* (2013.01)

(56) References Cited

U.S. PATENT DOCUMENTS

| | | | |
|---|---|---|---|
| 4,096,856 A | 6/1978 | Smith et al. | |
| 4,635,639 A | 1/1987 | Hakala et al. | |
| 4,916,439 A | 4/1990 | Estes et al. | |
| 5,012,411 A | 4/1991 | Policastro et al. | |
| 5,078,134 A | 1/1992 | Heilman et al. | |
| 5,105,821 A | 4/1992 | Reyes | |
| 5,311,449 A | 5/1994 | Adams | |
| 5,321,837 A * | 6/1994 | Daniel et al. | |
| 5,419,336 A | 5/1995 | Margison et al. | |
| 5,470,343 A | 11/1995 | Fincke et al. | |
| 5,549,115 A | 8/1996 | Morgan et al. | |
| 5,549,659 A | 8/1996 | Johansen et al. | |
| 5,565,759 A | 10/1996 | Dunstan | |
| 5,593,426 A | 1/1997 | Morgan et al. | |
| 5,674,252 A | 10/1997 | Morgan et al. | |
| 5,680,863 A | 10/1997 | Morgan et al. | |
| 5,683,423 A | 11/1997 | Post et al. | |
| 5,685,314 A | 11/1997 | Geheb et al. | |
| 5,715,823 A | 2/1998 | Wood et al. | |
| 5,724,985 A | 3/1998 | Snell | |
| 5,749,902 A | 5/1998 | Olson et al. | |
| 5,749,913 A | 5/1998 | Cole et al. | |
| 5,782,878 A | 7/1998 | Morgan et al. | |
| 5,787,155 A | 7/1998 | Luna et al. | |
| 5,814,089 A | 9/1998 | Stokes | |
| 5,836,993 A | 11/1998 | Cole et al. | |
| 5,857,967 A | 1/1999 | Frid et al. | |
| 5,879,374 A | 3/1999 | Powers et al. | |
| 5,891,046 A | 4/1999 | Cyrus et al. | |
| 5,891,049 A | 4/1999 | Cyrus et al. | |
| 5,899,866 A | 5/1999 | Cyrus et al. | |
| 5,921,938 A | 7/1999 | Aoyama et al. | |
| 5,929,601 A | 7/1999 | Kaib et al. | |
| 5,950,632 A | 9/1999 | Reber et al. | |
| 5,951,485 A | 9/1999 | Cyrus et al. | |
| D414,869 S | 10/1999 | Daynes et al. | |
| 5,999,493 A | 12/1999 | Olson et al. | |
| 6,024,699 A | 2/2000 | Surwit et al. | |
| 6,041,257 A | 3/2000 | MacDuff et al. | |
| 6,047,207 A | 4/2000 | MacDuff et al. | |
| 6,057,758 A | 5/2000 | Dempsey et al. | |
| 6,102,856 A * | 8/2000 | Groff et al. | 600/301 |
| 6,111,505 A | 8/2000 | Wagener et al. | |
| 6,134,468 A | 10/2000 | Morgan et al. | |
| 6,141,584 A | 10/2000 | Rockwell et al. | |
| 6,144,922 A | 11/2000 | Douglas et al. | |
| 6,150,951 A | 11/2000 | Olejniczak et al. | |
| 6,157,313 A | 12/2000 | Emmermann et al. | |
| 6,183,417 B1 | 2/2001 | Geheb et al. | |
| 6,188,407 B1 | 2/2001 | Smith | |
| 6,201,992 B1 | 3/2001 | Freeman et al. | |
| 6,223,077 B1 | 4/2001 | Schweizer et al. | |
| 6,275,737 B1 | 8/2001 | Mann | |
| 6,301,501 B1 | 10/2001 | Cronin et al. | |
| 6,301,502 B1 | 10/2001 | Owen et al. | |
| 6,304,780 B1 | 10/2001 | Owen et al. | |
| 6,321,113 B1 | 11/2001 | Parker et al. | |
| 6,323,782 B1 | 11/2001 | Stephens et al. | |
| 6,334,070 B1 | 12/2001 | Nova et al. | |
| 6,336,900 B1 | 1/2002 | Alleckson et al. | |
| D455,492 S | 4/2002 | Daynes et al. | |
| 6,370,428 B1 | 4/2002 | Snyder et al. | |
| 6,374,138 B1 | 4/2002 | Owen et al. | |
| 6,377,223 B1 | 4/2002 | Clapp et al. | |
| 6,381,492 B1 | 4/2002 | Rockwell et al. | |
| 6,402,691 B1 | 6/2002 | Peddicord et al. | |
| 6,405,083 B1 | 6/2002 | Rockwell et al. | |
| 6,422,669 B1 | 7/2002 | Salvatori | |
| 6,427,083 B1 | 7/2002 | Owen et al. | |
| 6,434,429 B1 | 8/2002 | Kraus et al. | |
| 6,438,417 B1 | 8/2002 | Rockwell et al. | |
| 6,441,747 B1 | 8/2002 | Khair et al. | |
| 6,493,581 B2 | 12/2002 | Russell et al. | |
| 6,524,241 B2 | 2/2003 | Iliff et al. | |
| 6,571,128 B2 | 5/2003 | Lebel et al. | |
| 6,591,135 B2 | 7/2003 | Palmer et al. | |
| 6,594,634 B1 | 7/2003 | Hampton et al. | |
| 6,597,948 B1 | 7/2003 | Rockwell et al. | |
| 6,668,192 B1 | 12/2003 | Parker et al. | |
| 6,771,172 B1 | 8/2004 | Robinson et al. | |
| 6,957,102 B2 | 10/2005 | Silver et al. | |
| 6,978,181 B1 | 12/2005 | Snell | |
| 7,006,865 B1 | 2/2006 | Cohen et al. | |
| 7,110,825 B2 | 9/2006 | Vaynberg et al. | |
| 7,570,994 B2 | 8/2009 | Tamura et al. | |
| 8,040,246 B2 | 10/2011 | Graves et al. | |
| D649,644 S | 11/2011 | Chai | |
| 8,054,177 B2 | 11/2011 | Graves et al. | |
| D658,296 S | 4/2012 | Matheson | |
| 8,154,246 B1 | 4/2012 | Heitmann | |
| D693,006 S | 11/2013 | Arimitsu | |
| 8,594,784 B2 | 11/2013 | Schwibner et al. | |
| 9,155,902 B2 | 10/2015 | Schwibner et al. | |
| 9,168,386 B2 | 10/2015 | Schwibner et al. | |
| 9,289,621 B2 | 3/2016 | Aoyama | |
| 2001/0041920 A1 | 11/2001 | Starkweather et al. | |
| 2002/0103508 A1 | 8/2002 | Mathur et al. | |
| 2002/0116028 A1 | 8/2002 | Greatbatch | |
| 2002/0116029 A1 | 8/2002 | Miller | |
| 2002/0116033 A1 | 8/2002 | Greatbatch | |
| 2002/0116034 A1 | 8/2002 | Miller | |
| 2002/0123673 A1 | 9/2002 | Webb et al. | |
| 2002/0128689 A1 | 9/2002 | Connelly | |
| 2002/0128691 A1 | 9/2002 | Connelly | |
| 2002/0133086 A1 | 9/2002 | Connelly | |
| 2002/0133199 A1 | 9/2002 | MacDonald | |
| 2002/0133200 A1 | 9/2002 | Weiner | |
| 2002/0133201 A1 | 9/2002 | Connelly | |
| 2002/0133202 A1 | 9/2002 | Connelly | |
| 2002/0133208 A1 | 9/2002 | Connelly | |

(56) References Cited

U.S. PATENT DOCUMENTS

| | | |
|---|---|---|
| 2002/0133211 A1 | 9/2002 | Weiner |
| 2002/0133216 A1 | 9/2002 | Connelly |
| 2002/0138102 A1 | 9/2002 | Weiner |
| 2002/0138103 A1 | 9/2002 | Mulhauser et al. |
| 2002/0138107 A1 | 9/2002 | Weiner |
| 2002/0138108 A1 | 9/2002 | Weiner |
| 2002/0138110 A1 | 9/2002 | Connelly |
| 2002/0138112 A1 | 9/2002 | Connelly |
| 2002/0138113 A1 | 9/2002 | Connelly |
| 2002/0138124 A1 | 9/2002 | Helfer |
| 2002/0143258 A1 | 10/2002 | Weiner |
| 2002/0147470 A1 | 10/2002 | Weiner |
| 2002/0177793 A1 | 11/2002 | Sherman et al. |
| 2002/0183796 A1 | 12/2002 | Connelly |
| 2002/0198569 A1 | 12/2002 | Foster |
| 2003/0025602 A1 | 2/2003 | Medema et al. |
| 2003/0028219 A1 | 2/2003 | Powers |
| 2003/0045905 A1 | 3/2003 | Daynes et al. |
| 2003/0050538 A1 | 3/2003 | Naghavi et al. |
| 2003/0058097 A1 | 3/2003 | Saltzstein et al. |
| 2003/0088275 A1 | 5/2003 | Palmer et al. |
| 2003/0097160 A1 | 5/2003 | Caby et al. |
| 2003/0109904 A1 | 6/2003 | Silver et al. |
| 2003/0167074 A1 | 9/2003 | Merry |
| 2003/0212311 A1 | 11/2003 | Nova et al. |
| 2004/0049233 A1 | 3/2004 | Edwards |
| 2004/0096808 A1 | 5/2004 | Price et al. |
| 2004/0102167 A1 | 5/2004 | Shim |
| 2004/0111122 A1 | 6/2004 | Daynes et al. |
| 2004/0122476 A1 | 6/2004 | Wung |
| 2004/0162586 A1 | 8/2004 | Covey et al. |
| 2004/0204743 A1 | 10/2004 | McGrath et al. |
| 2005/0075671 A1 | 4/2005 | Vaisnys et al. |
| 2005/0124866 A1 | 6/2005 | Elaz et al. |
| 2005/0288571 A1* | 12/2005 | Perkins et al. ............... 600/407 |
| 2006/0069326 A1 | 3/2006 | Heath |
| 2006/0142808 A1 | 6/2006 | Pearce et al. |
| 2006/0149321 A1 | 7/2006 | Merry et al. |
| 2006/0149323 A1 | 7/2006 | Merry et al. |
| 2006/0173498 A1 | 8/2006 | Banville |
| 2007/0213775 A1 | 9/2007 | Snyder |
| 2008/0077185 A1 | 3/2008 | Pearce et al. |
| 2008/0183229 A1 | 7/2008 | Neumiller et al. |
| 2008/0221397 A1 | 9/2008 | McMahon et al. |
| 2008/0221930 A1 | 9/2008 | Wekell |
| 2009/0089078 A1* | 4/2009 | Bursey ............................. 705/1 |
| 2009/0264948 A1 | 10/2009 | Tamura et al. |
| 2009/0274384 A1* | 11/2009 | Jakobovits .................. 382/254 |
| 2009/0295326 A1 | 12/2009 | Daynes et al. |
| 2010/0114236 A1 | 5/2010 | Jiang et al. |
| 2010/0131482 A1* | 5/2010 | Linthicum et al. .......... 707/706 |
| 2010/0185547 A1* | 7/2010 | Scholar ............................ 705/80 |
| 2011/0153343 A1* | 6/2011 | Tremblay .............. G06F 19/327 |
| | | 705/2 |
| 2011/0172550 A1 | 7/2011 | Martin et al. |
| 2011/0208259 A1 | 8/2011 | Pearce et al. |
| 2011/0295078 A1 | 12/2011 | Reid et al. |
| 2012/0123223 A1* | 5/2012 | Freeman et al. ............. 600/301 |
| 2012/0172700 A1* | 7/2012 | Krishnan et al. ............ 600/407 |
| 2012/0239420 A1* | 9/2012 | Stapelfeldt et al. ............. 705/2 |
| 2012/0239428 A1* | 9/2012 | James et al. ..................... 705/3 |
| 2013/0093829 A1* | 4/2013 | Rosenblatt ............... G09B 5/00 |
| | | 348/14.01 |
| 2013/0096649 A1 | 4/2013 | Martin et al. |
| 2013/0231947 A1 | 9/2013 | Shusterman |

FOREIGN PATENT DOCUMENTS

| | | |
|---|---|---|
| EP | 1228782 | 8/2002 |
| EP | 1250944 | 10/2002 |
| WO | WO0070889 | 11/2000 |
| WO | WO0166182 | 9/2001 |
| WO | WO02/060529 | 8/2002 |
| WO | 2004093979 A1 | 4/2004 |
| WO | WO2005058416 | 6/2005 |
| WO | 2013056194 A1 | 4/2013 |
| WO | WO03009895 | 6/2013 |
| WO | WO2005058413 | 6/2015 |

OTHER PUBLICATIONS

Int'l Search Report and Written Opinion, PCT/US2012/071461, mailed Apr. 10, 2013, 14 pages.
Int'l Search Report and Written Opinion, PCT/US2012/071488, mailed Feb. 8, 2013, 11 pages.
ISR and Written Opinion, PCT/US12/71450, issued May 24, 2013 (10 pages).
U.S. Appl. No. 60/464,860, filed Apr. 22, 2003, Christopher Pearce et al., 7 pages.
U.S. Appl. No. 60/530,151, filed Dec. 17, 2003, Christopher Pearce et al., 125 pages.
International Search Report & Written Opinion dated Jan. 25, 2016, International Application No. PCT/US15/055095, international filing date Oct. 12, 2015.
International Search Report and Written Opinion, PCT/US2012/071448, dated Feb. 8, 2013, 11 pages.
Claims of U.S. Appl. No. 15/057,468 dated Jul. 8, 2016.
Office Action dated Mar. 4, 2016, U.S. Appl. No. 13/690,075, filed Nov. 30, 2012.
Office Action dated Jul. 15, 2015, U.S. Appl. No. 13/690,075, filed Nov. 30, 2012.
Final Office Action dated Oct. 18, 2016, U.S. Appl. No. 13/690,075, filed Nov. 30, 2012.
Final Office Action dated Jan. 13, 2016, U.S. Appl. No. 13/690,075, filed Nov. 30, 2012.
Final Office Action dated Mar. 24, 2014, U.S. Appl. No. 13/690,094, filed Nov. 30, 2012.
Final Office Action dated Mar. 3, 2015, U.S. Appl. No. 13/690,094, filed Nov. 30, 2012.
Office Action dated Sep. 26, 2013, U.S. Appl. No. 13/690,094, filed Nov. 30, 2012.
Office Action dated Sep. 24, 2014, U.S. Appl. No. 13/690,094, filed Nov. 30, 2012.
Office Action dated Jul. 14, 2015, U.S. Appl. No. 13/690,094, filed Nov. 30, 2012.
Final Office Action dated Jan. 14, 2016, U.S. Appl. No. 13/690,056, filed Nov. 30, 2012.
Office Action dated Aug. 10, 2015, U.S. Appl. No. 13/690,056, filed Nov. 30, 2012.
Office Action dated Mar. 7, 2016, U.S. Appl. No. 13/690,056, filed Nov. 30, 2012.
Office Action dated Sep. 1, 2016, U.S. Appl. No. 13/690,056, filed Nov. 30, 2012.
Office Action dated Nov. 15, 2016, U.S. Appl. No. 13/690,056, filed Nov. 30, 2012.
Office Action dated Mar. 7, 2017, U.S. Appl. No. 13/690,056, filed Nov. 30, 2012.
Office Action dated Nov. 23, 2016, U.S. Appl. No. 15/152,248, filed May 11, 2016.
Office Action dated Aug. 18, 2014, U.S. Appl. No. 29/452,640, filed Apr. 19, 2013.
Office Action dated Aug. 18, 2014, U.S. Appl. No. 29/440,594, filed Dec. 21, 2012.
Final Office Action dated Jan. 8, 2016, U.S. Appl. No. 13/690,031, filed Nov. 30, 2012.
Office Action dated Jul. 15, 2015, U.S. Appl. No. 13/690,031, filed Nov. 30, 2012.
Notice of Allowance, dated Sep. 3, 2013, U.S. Appl. No. 10/583,176, filed Mar. 5, 2008.
Amendment, dated Jul. 11, 2013, U.S. Appl. No. 10/583,176, filed Mar. 5, 2008.
Non-Final Rejection, dated Jan. 16, 2013, U.S. Appl. No. 10/583,176, filed Mar. 5, 2008.
Amendment, dated Oct. 1, 2012, U.S. Appl. No. 10/583,176, filed Mar. 5, 2008.

(56) References Cited

OTHER PUBLICATIONS

Non-Final Rejection, dated May 1, 2012, U.S. Appl. No. 10/583,176, dated Mar. 5, 2008.
Amendment, dated Apr. 5, 2012, U.S. Appl. No. 10/583,176, filed Mar. 5, 2008.
Final Rejection, dated Nov. 17, 2011, U.S. Appl. No. 10/583,176, filed Mar. 5, 2008.
Amendment, dated Aug. 22, 2011, U.S. Appl. No. 10/583,176, filed Mar. 5, 2008.
Non-Final Rejection, dated May 20, 2011, U.S. Appl. No. 10/583,176, filed Mar. 5, 2008.
Notice of Allowance, dated Jan. 26, 2011, U.S. Appl. No. 10/583,209, filed Oct. 18, 2007.
Amendment, dated Jan. 26, 2011, U.S. Appl. No. 10/583,209, filed Oct. 18, 2007.
Amendment, dated Dec. 20, 2010, U.S. Appl. No. 10/583,209, filed Oct. 18, 2007.
Final Rejection, dated Oct. 19, 2010, U.S. Appl. No. 10/583,209, filed Oct. 18, 2007.
Amendment, dated Jun. 16, 2010, U.S. Appl. No. 10/583,209, filed Oct. 18, 2007.
Non-Final Rejection, dated Mar. 16, 2010, U.S. Appl. No. 10/583,209, filed Oct. 18, 2007.
Non-Final Rejection, dated Feb. 3, 2011, U.S. Appl. No. 11/256,275, filed Oct. 21, 2005.
Amendment, dated Apr. 20, 2010, U.S. Appl. No. 11/256,275, filed Oct. 21, 2005.
Final Rejection, dated Feb. 3, 2010, U.S. Appl. No. 11/256,275, filed Oct. 21, 2005.
Amendment, dated Sep. 9, 2009, U.S. Appl. No. 11/256,275, filed Oct. 21, 2005.
Non-Final Rejection, dated Jun. 9, 2009, U.S. Appl. No. 11/256,275, filed Oct. 21, 2005.
Amendment, dated Apr. 3, 2009, U.S. Appl. No. 11/256,275, filed Oct. 21, 2005.
Final Rejection, dated Jan. 6, 2009, U.S. Appl. No. 11/256,275, filed Oct. 21, 2005.
Amendment, dated Oct. 8, 2008, U.S. Appl. No. 11/256,275, dated Oct. 21, 2005.
Non-Final Rejection, dated Jun. 9, 2008, U.S. Appl. No. 11/256,275, filed Oct. 21, 2005.
Response to Restriction, dated May 14, 2008, U.S. Appl. No. 11/256,275, filed Oct. 21, 2005.
Restriction Requirement, dated Feb. 5, 2008, U.S. Appl. No. 11/256,275, filed Oct. 21, 2005.
Preliminary Amendment, dated Sep. 26, 2014, U.S. Appl. No. 14/498,735, filed Sep. 26, 2014.
Notice of Allowance, dated May 11, 2016, U.S. Appl. No. 14/498,735, filed Sep. 26, 2014.
Amendment, dated Dec. 31, 2015, U.S. Appl. No. 14/498,735, filed Sep. 26, 2014.
Non-Final Rejection, dated Sep. 15, 2015, U.S. Appl. No. 14/498,735, filed Sep. 26, 2014.
Non-Final Rejection, dated Mar. 9, 2017, U.S. Appl. No. 14/069,021, filed Oct. 31, 2013.
Notice of Allowance, dated Mar. 14, 2014, U.S. Appl. No. 10/583,175, filed Nov. 1, 2007.
Amendment, dated Feb. 11, 2014, U.S. Appl. No. 10/583,175, filed Nov. 1, 2007.
Non-Final Rejection, dated Nov. 22, 2013, U.S. Appl. No. 10/583,175, filed Nov. 1, 2007.
Advisory Action, dated Oct. 10, 2013, U.S. Appl. No. 10/583,175, dated Nov. 1, 2007.
Amendment, dated Sep. 27, 2013, U.S. Appl. No. 10/583,175, filed Nov. 1, 2007.
Final Rejection, dated Jul. 29, 2013, U.S. Appl. No. 10/583,175, filed Nov. 1, 2007.
Amendment, dated Jun. 14, 2013, U.S. Appl. No. 10/583,175, filed Nov. 1, 2007.
Non-Final Rejection, dated Feb. 28, 2013, U.S. Appl. No. 10/583,175, filed Nov. 1, 2007.
Amendment, dated Jul. 29, 2010, U.S. Appl. No. 10/583,175, filed Nov. 1, 2007.
Final Rejection, dated Apr. 29, 2010, U.S. Appl. No. 10/583,175, filed Nov. 1, 2007.
Amendment, dated Jan. 4, 2010, U.S. Appl. No. 10/583,175, filed Nov. 1, 2007.
Non-Final Rejection, dated Oct. 2, 2009, U.S. Appl. No. 10/583,175, filed Nov. 1, 2007.
Notice of Allowance, dated Jun. 26, 2014, U.S. Appl. No. 13/965,667, filed Aug. 13, 2013.
Amendment, dated Jun. 26, 2014, U.S. Appl. No. 13/965,667, filed Aug. 13, 2013.
Response, dated May 28, 2014, U.S. Appl. No. 13/965,667, filed Aug. 13, 2013.
Final Rejection, dated Feb. 28, 2014, U.S. Appl. No. 13/965,667, filed Aug. 13, 2013.
Amendment, dated Feb. 5, 2014, U.S. Appl. No. 13/965,667, filed Aug. 13, 2013.
Non-Final Rejection, dated Nov. 5, 2013, U.S. Appl. No. 13/965,667, filed Aug. 13, 2013.
Final Rejection, dated Dec. 2, 2015, U.S. Appl. No. 14/069,021, filed Oct. 31, 2013.
Amendment, dated Sep. 23, 2015, U.S. Appl. No. 14/069,021, filed Oct. 31, 2013.
Non-Final Action, dated Mar. 23, 2015, U.S. Appl. No. 14/069,021, filed Oct. 31, 2013.
Amendment, dated Jan. 21, 2015, U.S. Appl. No. 14/069,021, filed Oct. 31, 2013.
Non-Final Rejection, dated Oct. 21, 2014, U.S. Appl. No. 14/069,021, filed Oct. 31, 2013.
Notice of Allowance dated May 9, 2013, U.S. Appl. No. 13/103,783, filed May 9, 2011.
Amendment, dated May 9, 2013, U.S. Appl. No. 13/103,783, May 9, 2011.
Response, dated May 2, 2013, U.S. Appl. No. 13/103,783, filed May 9, 2011.
Final Rejection, dated Feb. 1, 2013, U.S. Appl. No. 13/103,783, filed May 9, 2011.
Amendment, dated Feb. 28, 2012, U.S. Appl. No. 13/103,783, filed May 9, 2011.
Non-Final Rejection, dated Nov. 28, 2011, U.S. Appl. No. 13/103,783, filed May 9, 2011.
Preliminary Amendment, dated Jun. 8, 2011, U.S. Appl. No. 13/103,783, filed May 9, 2011.
Non-Final Rejection, dated Nov. 1, 2016, U.S. Appl. No. 14/310,841, filed Jun. 20, 2014.
Amendment, dated Sep. 27, 2016, U.S. Appl. No. 14/310,841, filed Jun. 20, 2014.
Final Rejection, dated Jul. 7, 2016, U.S. Appl. No. 14/310,841, filed Jun. 20, 2014.
Amendment, dated May 25, 2016, U.S. Appl. No. 14/310,841, filed Jun. 20, 2014.
Non-Final Rejection, dated Feb. 8, 2016, U.S. Appl. No. 14/310,841, filed Jun. 20, 2014.
Response, dated Jan. 11, 2016, U.S. Appl. No. 14/310,841, filed Jun. 20, 2014.
Requirement for Restriction/Election dated Nov. 9, 2015, U.S. Appl. No. 14/310,841, dated Jun. 20, 2014.
International Search Report and Written Opinion from International Application No. PCT/US2004/042376, dated Mar. 24, 2005.
International Preliminary Report on Patentability from International Application No. PCT/US2004/042376, dated Jun. 20, 2006.
International Search Report and Written Opinion from International Application No. PCT/US2004/042792, dated Jul. 20, 2005.
International Preliminary Report on Patentability from International Appliction No. PCT/US2004/042792, dated Jun. 20, 2006.
International Search Report and Written Opinion from International Appliction No. PCT/US2004/012421, dated Sep. 13, 2004.
International Preliminary Report on Patentability from International Appliction No. PCT/US2004/012421, dated Oct. 28, 2005.

(56) References Cited

OTHER PUBLICATIONS

International Search Report and Written Opinion from International Appliction No. PCT/US2004/042377, dated Jun. 20, 2006.
Notice of Allowance, dated Mar. 21, 2016, U.S. Appl. No. 13/690,031, filed Nov. 30, 2012.
Amendment, dated Aug. 25, 2016, U.S. Appl. No. 13/690,031, filed Nov. 30, 2012.
Amendment, dated May 11, 2016, U.S. Appl. No. 13/690,031, filed Nov. 30, 2012.
Preliminary Amendment, dated Aug. 14, 2013, U.S. Appl. No. 13/690,031, Nov. 30, 2012.
Prelimianry Amendment, dated Aug. 14, 2013, U.S. Appl. No. 13/690,031, filed Nov. 30, 2012.
Amendment, dated Aug. 23, 2016, U.S. Appl. No. 13/690,031, filed Nov. 30, 2012.
Amendment, dated Oct. 5, 2015, U.S. Appl. No. 13/690,031, filed Nov. 30, 2012.
Preliminary Amendment, dated Jan. 9, 2017, U.S. Appl. No. 15/283,966, filed Oct. 3, 2016.
Preliminary Amendment, dated Oct. 28, 2016, U.S. Appl. No. 15/283,966, filed Oct. 3, 2016.
Non-Final Action, dated Mar. 13, 2017, U.S. Appl. No. 15/057,468, filed Mar. 1, 2016.
Non-Final Action, dated Apr. 14, 2016, U.S. Appl. No. 15/057,468, filed Mar. 1, 2016.
Notice of Allowance, dated Jan. 13, 2017, U.S. Appl. No. 15/057,468, filed Mar. 1, 2016.
Notice of Allowance, dated Nov. 21, 2016, U.S. Appl. No. 15/057,468, filed Mar. 1, 2016.
Notice of Allowance, dated Aug. 31, 2016, U.S. Appl. No. 15/057,468, filed Mar. 1, 2016.
Amendment, dated Jan. 13, 2017, U.S. Appl. No. 15/057,468, filed Mar. 1, 2016.
Amendment, dated Nov. 21, 2016, U.S. Appl. No. 15/057,468, filed Mar. 1, 2016.
Amendment, dated Jan. 6, 2017, U.S. Appl. No. 15/057,468, filed Mar. 1, 2016.
Amendment, dated Oct. 31, 2016, U.S. Appl. No. 15/057,468, filed Mar. 1, 2016.
Amendment, dated Jul. 8, 2016, U.S. Appl. No. 15/057,468, filed Mar. 1, 2016.
Notice of Allowance, dated Feb. 8, 2017, U.S. Appl. No. 13/690,075, filed Nov. 30, 2012.
Response to Restriction, dated Oct. 28, 2014, U.S. Appl. No. 13/690,075, filed Nov. 30, 2012.
Restriction Requirement, dated Oct. 20, 2014, U.S. Appl. No. 13/690,075, filed Nov. 30, 2012.
Amendment, dated Jan. 27, 2017, U.S. Appl. No. 13/690,075, filed Nov. 30, 2012.
Preliminary Amendment, dated Aug. 14, 2013, U.S. Appl. No. 13/690,075, filed Nov. 30, 2012.
Preliminary Amendment, dated Nov. 18, 2016, U.S. Appl. No. 13/690,075, filed Nov. 30, 2012.
Amendment, dated Jun. 15, 2016, U.S. Appl. No. 13/836,769, filed Mar. 15, 2013.
Amendment, dated Oct. 5, 2015, U.S. Appl. No. 13/690,075, filed Nov. 30, 2012.
Amendment After Notice of Allowance, dated Mar. 16, 2017, U.S. Appl. No. 13/690,075, filed Nov. 30, 2012.
Notice of Allowance, dated Feb. 18, 2016, U.S. Appl. No. 13/690,094, filed Nov. 30, 2012.
Notice of Allowance, dated Nov. 9, 2015, U.S. Appl. No. 13/690,094, filed Nov. 30, 2012.
Advisory Action, dated May 12, 2015, U.S. Appl. No. 13/690,094, filed Nov. 30, 2012.
Amendment, dated Feb. 18, 2016, U.S. Appl. No. 13/690,094, filed Nov. 30, 2012.
Amendment, dated May 12, 2015, U.S. Appl. No. 13/690,094, filed Nov. 30, 2012.
Amendment, dated Jun. 2, 2015, U.S. Appl. No. 13/690,094, filed Nov. 30, 2012.
Preliminary Amendment, dated Aug. 14, 2013, U.S. Appl. No. 13/690,094, filed Nov. 30, 2012.
Response, dated Apr. 29, 2015, U.S. Appl. No. 13/690,094, filed Nov. 30, 2012.
Amendment, dated Feb. 5, 2016, U.S. Appl. No. 13/690,094, filed Nov. 30, 2012.
Amendment, dated Oct. 14, 2015, U.S. Appl. No. 13/690,094, filed Nov. 30, 2012.
Amendment, dated Jan. 19, 2015, U.S. Appl. No. 13/690,094, filed Nov. 30, 2012.
Amendment, dated Dec. 18, 2013, U.S. Appl. No. 13/690,094, filed Nov. 30, 2012.
Amendment, dated Oct. 28, 2016, U.S. Appl. No. 13/690,056, filed Nov. 30, 2012.
Amendment, dated Jun. 6, 2016, U.S. Appl. No. 13/690,056, filed Nov. 30, 2012.
Amendment, dated Oct. 5, 2015, U.S. Appl. No. 13/690,056, filed Nov. 30, 2012.
Preliminary Amendment, dated Aug. 14, 2013, U.S. Appl. No. 13/690,056, filed Nov. 30, 2012.
Amendment, dated Mar. 15, 2017, U.S. Appl. No. 13/690,056, filed Nov. 30, 2012.
Amendment, dated Nov. 28, 2016, U.S. Appl. No. 13/690,056, filed Nov. 30, 2012.
Preliminary Amendment, dated Jan. 9, 2017, U.S. Appl. No. 15/152,248, filed May 11, 2016.
Preliminary Amendment, dated Oct. 28, 2016, U.S. Appl. No. 15/152,248, filed May 11, 2016.
Amendment, dated Mar. 23, 2017, U.S. Appl. No. 15/152,248, filed May 11, 2016.
Notice of Allowance, dated Nov. 19, 2014, U.S. Appl. No. 29/452,640, filed Apr. 19, 2013.
Non-Final Rejection, dated Aug. 18, 2014, U.S. Appl. No. 29/452,640, filed Apr. 19, 2013.
Amendment, dated Nov. 3, 2014, U.S. Appl. No. 29/452,640, filed Apr. 19, 2013.
Amendment, dated Oct. 1, 2014, U.S. Appl. No. 29/452,640, filed Apr. 19, 2013.
Notice of Allowance, dated Nov. 28, 2014, U.S. Appl. No. 29/440,594, filed Dec. 21, 2012.
Response, dated Aug. 7, 2014, U.S. Appl. No. 29/440,594, filed Dec. 21, 2012.
Amendment, dated Nov. 3, 2014, U.S. Appl. No. 29/440,594, filed Dec. 21, 2012.
Amendment, dated Oct. 1, 2014, U.S. Appl. No. 29/440,594, filed Dec. 21, 2012.
Notice of Allowance, dated Jun. 7, 2016, U.S. Appl. No. 13/690.031, filed Nov. 30, 2012.
International Preliminary Report on Patentability dated Apr. 18, 2016, International Application No. PCT/US15/055095, international filing date Oct. 12, 2015.
International Preliminary Report on Patentability dated Nov. 11, 2014, PCT/US2012/071436, dated Apr. 10, 2013.
International Preliminary Report on Patentability dated Nov. 11, 2014, PCT/US2012/071461, dated Apr. 10, 2013, 14 pages.
International Preliminary Report on Patentability dated Nov. 11, 2014, PCT/US2012/071448, dated Feb. 8, 2013, 11 pages.
International Preliminary Report on Patentability dated Nov. 11, 2014, PCT/US2012071450, dated May 24, 2013.
RCE_Amendment dated, dated Apr. 12, 2017, U.S. Appl. No. 13/690,075, filed Nov. 30, 2012.
Notice of Allowance, dated May 5, 2017, U.S. Appl. No. 13/690,075, filed Nov. 30, 2012.
Notice of Allowance dated Jun. 14, 2017, U.S. Appl. No. 13/690,056, filed Nov. 30, 2012.
Final Office Action dated May 12, 2017, U.S. Appl. No. 15/152,248, filed May 11, 2016.
Amendment, dated May 17, 2017, U.S. Appl. No. 14/069,021, filed Oct. 31, 2013.

(56) References Cited

OTHER PUBLICATIONS

International Preliminary Examination Report, dated Nov. 12, 2004, International Application No. PCT/US03/28463, International Filing Date Sep. 9, 2003.
Non-Final Rejection dated Jun. 14, 2017, U.S. Appl. No. 12/139,359, filed Jun. 13, 2008.
Amendment dated Apr. 19, 2017, U.S. Appl. No. 12/139,359, filed Jun. 13, 2008.
Advisory Action dated Mar. 31, 2017, U.S. Appl. No. 12/139,359, filed Jun. 13, 2008.
Amendment After Final dated Mar. 31, 2017, U.S. Appl. No. 12/139,359, filed Jun. 13, 2008.
Response After Final Action dated Mar. 23, 2017, U.S. Appl. No. 12/139,359, filed Jun. 13, 2008.
Final Rejection dated Nov. 23, 2016, U.S. Appl. No. 12/139,359, filed Jun. 13, 2008.
Amendment dated Sep. 14, 2016, U.S. Appl. No. 12/139,359, filed Jun. 13, 2008.
Non-Final Rejection dated Jun. 15, 2016, U.S. Appl. No. 12/139,359, filed Jun. 13, 2008.
Amendment dated Mar. 15, 2016, U.S. Appl. No. 12/139,359, filed Jun. 13, 2008.
Final Rejection dated Dec. 15, 2015, U.S. Appl. No. 12/139,359, filed Jun. 13, 2008.
Amendment dated Sep. 29, 2015, U.S. Appl. No. 12/139,359, filed Jun. 13, 2008.
Non-Final Rejection dated Jun. 29, 2015, U.S. Appl. No. 12/139,359, filed Jun. 13, 2008.
Amendment dated May 26, 2015, U.S. Appl. No. 12/139,359, filed Jun. 13, 2008.
Final Rejection dated Mar. 22, 2011, U.S. Appl. No. 12/139,359, filed Jun. 13, 2008.
Amendment dated Jan. 5, 2011, U.S. Appl. No. 12/139,359, filed Jun. 13, 2008.
Non-Final Rejection dated Oct. 5, 2011, U.S. Appl. No. 12/139,359, filed Jun. 13, 2008.
Final Rejection dated Aug. 2, 2006, U.S. Appl. No. 10/378,001, filed Feb. 28, 2003.
Amendment dated May 30, 2006, U.S. Appl. No. 10/378,001, filed Feb. 28, 2003.
Non-Final Rejection dated Dec. 27, 2005, U.S. Appl. No. 10/378,001, filed Feb. 28, 2003.
Response to Rejection dated Nov. 21, 2005, U.S. Appl. No. 10/378,001, filed Feb. 28, 2003.
Requirement for Restriction dated Oct. 21, 2005, U.S. Appl. No. 10/378,001, filed Feb. 28, 2003.
Communication from the Examining Division dated Aug. 18, 2008, Application No. EP1617896.
Reply to Communication from the Examining Division dated Dec. 16, 2008, Application No. EP1617896.
Decision to Grant dated Aug. 6, 2009, Application No. EP1617896.
Communication from the Examining Division dated Jun. 29, 2017, Application No. EP12816583.4.
Amendment, dated Jul. 13, 2017, U.S. Appl. No. 15/057,468 filed Mar. 1, 2016.
Amendment filed Mar. 19, 2018, U.S. Appl. No. 13/836,769, filed Mar. 15, 2013.
Office Action dated Oct. 19, 2017, U.S. Appl. No. 13/836,769, filed Mar. 15, 2013.
Final Office Action dated Mar. 19, 2018, U.S. Appl. No. 13/690,075, filed Nov. 30, 2012.
Amendment dated Dec. 21, 2017, U.S. Appl. No. 13/690,075, filed Nov. 30, 2012.
Office Action dated Aug. 21, 2017, U.S. Appl. No. 13/690,075, filed Nov. 30, 2012.
Notice of Allowance dated Jan. 19, 2018, U.S. Appl. No. 13/690,056, filed Nov. 30, 2012.
Notice of Allowance dated Jan. 31, 2018, U.S. Appl. No. 15/152,248, filed May 11, 2016.
Response dated Oct. 12, 2017, U.S. Appl. No. 15/152,248, filed May 11, 2016.
Final Rejection dated Nov. 16, 2017, U.S. Appl. No. 14/069,021, filed Oct. 31, 2013.
International Preliminary Report of Patentability dated Jun. 20, 2006, from International Application No. PCT/US2004/042377, dated Jun. 20, 2006.
Amendment filed Mar. 13, 2018, U.S. Appl. No. 15/245,450, filed Aug. 24, 2016.
Non-Final Office Action dated Dec. 15, 2017, U.S. Appl. No. 15/245,450, filed Aug. 24, 2016.
Final Rejection dated Jan. 11, 2018, U.S. Appl. No. 12/139,359, filed Jun. 13, 2008.
Amendment dated Apr. 11, 2018, U.S. Appl. No. 12/139,359, filed Jun. 13, 2008.
Amendment dated Dec. 14, 2017, U.S. Appl. No. 12/139,359, filed Jun. 13, 2008.
Amendment filed Sep. 14, 2018, U.S. Appl. No. 14/069,021, filed Oct. 31, 2013.
NonFinal Office Action dated Sep. 20, 2018, U.S. Appl. No. 12/139,359, filed Jun. 13, 2008.
Final Office Action dated Jul. 13, 2018, U.S. Appl. No. 15/245,450, filed Aug. 24, 2016.
Notice of Allowance dated Jul. 13, 2018, U.S. Appl. No. 13/690,075, filed Nov. 30, 2012.
Notice of Allowance dated Jul. 13, 2018, U.S. Appl. No. 15/152,248 filed May 11, 2016.
Notice of Allowance dated Jun. 21, 2018, U.S. Appl. No. 15/283,966, filed Oct. 3, 2016.
Office Action dated Jun. 14, 2018, U.S. Appl. No. 14/069,021, dated Oct. 31, 2013.
Notice of Allowance dated Aug. 15, 2018, U.S. Appl. No. 15/245,450, filed Aug. 24, 2016.
Response to Final Office Action dated Jul. 27, 2018, U.S. Appl. No. 15/245,450, filed Aug. 24, 2016.

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

DECISION SUPPORT TOOL FOR USE WITH A MEDICAL MONITOR-DEFIBRILLATOR

CROSS REFERENCE TO RELATED PATENT APPLICATIONS

This patent application may be found to be related to U.S. patent application Ser. No. 13/836,304, entitled "Clinical Dashboard for Medical Device", filed contemporaneously on Mar. 15, 2013, in the name of Randy L. Merry et al.; and U.S. patent application Ser. No. 13/839,859, entitled "Medical Monitor-Defibrillator with Defibrillator and Data Operations Processors", filed contemporaneously on Mar. 15, 2013, in the name of Ken Peterson et al.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

Advanced medical devices may be used to assist the CPR process by coaching a rescuer who performs CPR. For example, a medical device can issue instructions, and even prompts, for the rescuer to perform CPR more effectively.

While some advanced medical devices provide coaching, defibrillator operators may benefit from additional coaching.

BRIEF SUMMARY

The present description gives instances of devices, systems, software and methods, the use of which may help overcome problems and limitations of the prior art.

More specifically, work flows are modeled as a graph of interdependent tasks to be performed. The tasks to be performed are set by a task file module configured to enable interactions between tasks and including modules for event viewing, protocol assistance, smart messaging, smart indices, reference material lookup. A decision support manager module is configured to construct data and model profiles for storage in a data and model profile bank, events for storage in a decision support events bank, and protocols for storage in a decision support protocol bank. Configuration files are provided to specify a configuration for execution of one of the tasks. Data entered through a user interface or from a network via a wireless or wired communication module may define task files in the task files module, configuration files in the configuration files module, as well as data, events, and protocols to be used for a defibrillation procedure. A decision support manager module is configured to construct a dependency graph of tasks as specified in at least one of the configuration files and to execute the dependency graph.

These and other features and advantages of this description will become more readily apparent from the following Detailed Description, which proceeds with reference to the drawings, in which:

BRIEF DESCRIPTION OF THE DRAWINGS

FIG. 1 is an illustrative diagram of a scene showing the use of an external defibrillator to save the life of a person according to this disclosure.

FIG. 2 is a table listing two illustrative types of the external defibrillator shown in FIG. 1, and who they might be used by.

DETAILED DESCRIPTION

Figures 1, 2:
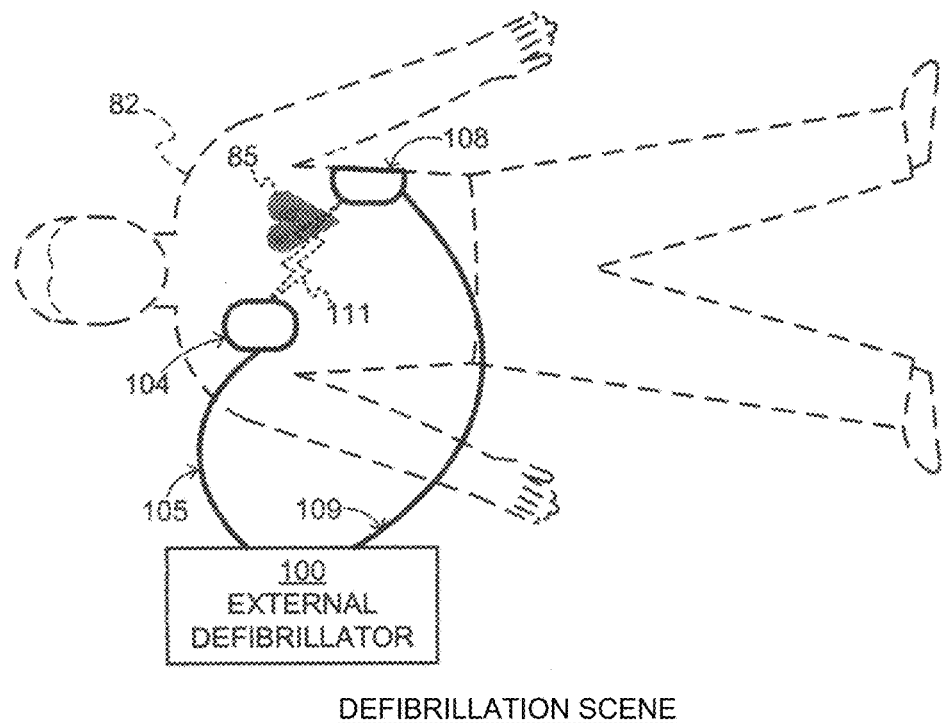

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
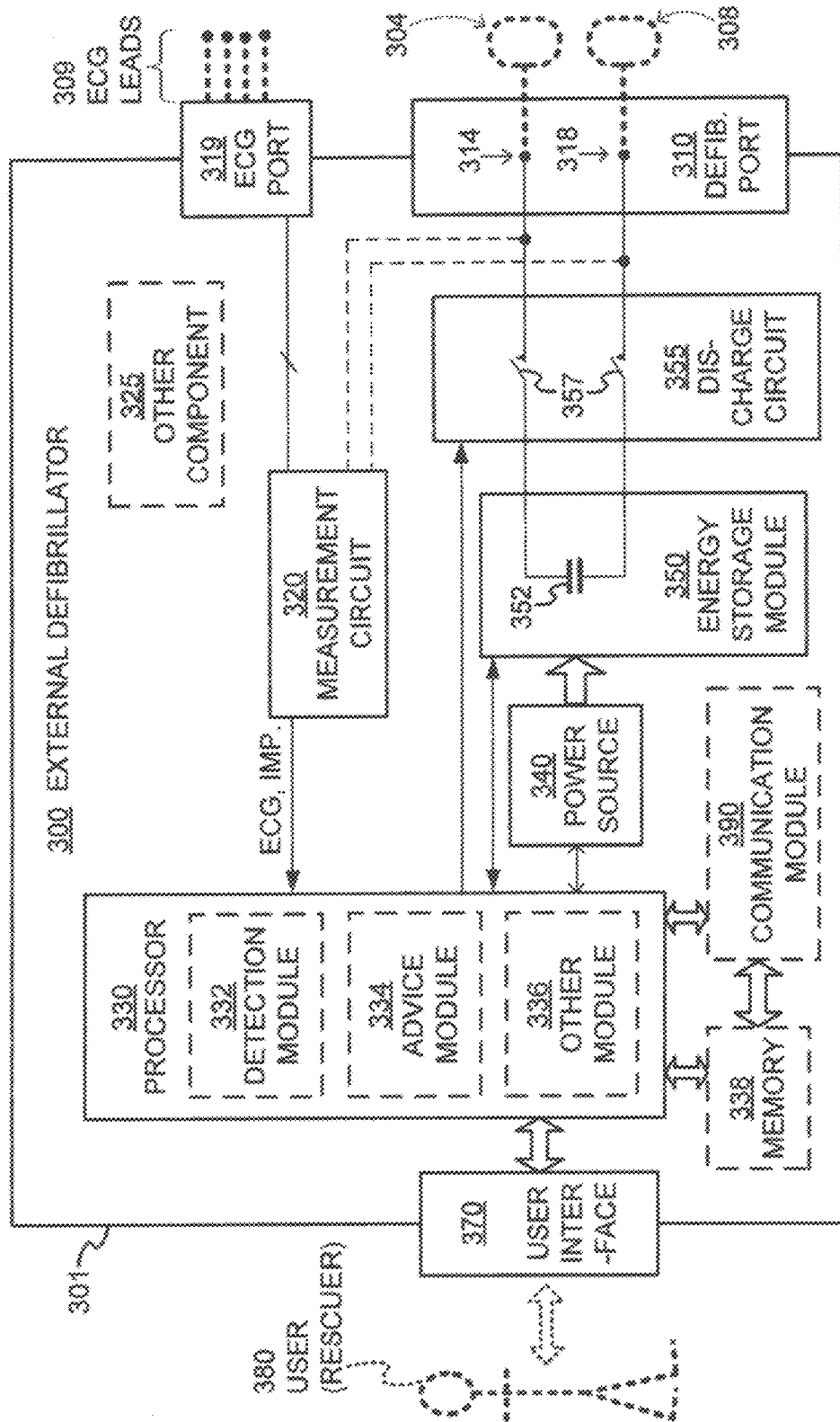
FIG. 3 is a diagram showing components of an external defibrillator, such as the one shown in FIG. 1, configured in an illustrative embodiment according to this disclosure.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Having thus introduced background on the general operation of a defibrillator, we now turn to features that are provided by this disclosure.

Figure 4:
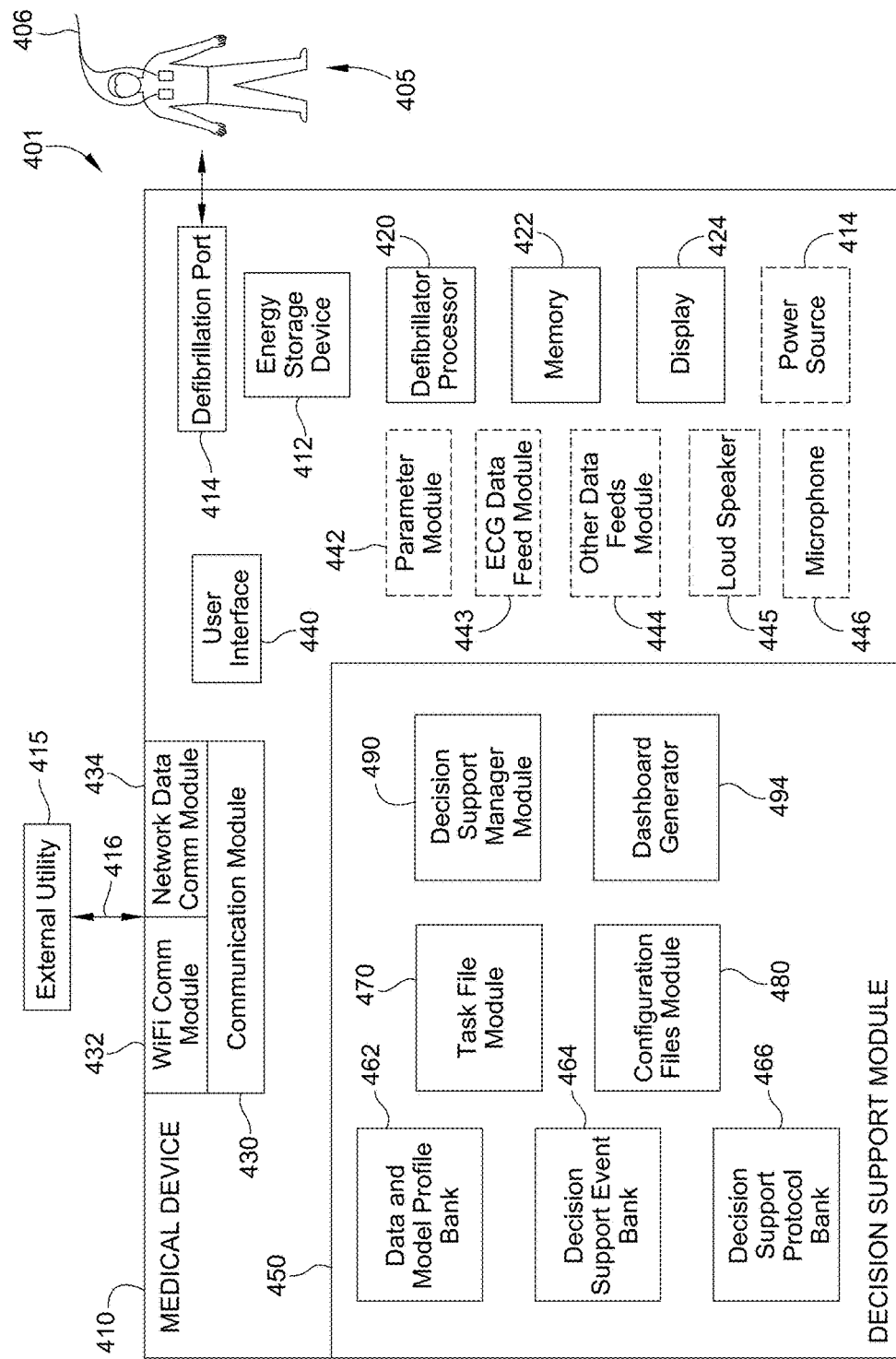
FIG. 4 shows a functional diagram of an illustrative system for providing decision support to a caregiver according to this disclosure.

FIG. 4 shows a functional diagram of an illustrative system for providing decision support to a caregiver according to this disclosure. The defibrillator system comprises a defibrillator 410, a defibrillation site 405, and an external utility 415.

The defibrillation site 405 is a subject being administered a defibrillator charge through contact electrode pair 406 by a caregiver. The electrode pair (electrodes 104, 108 in FIG. 1) is attached to the skin of a person on one end. The electrode pair is tethered by hard-wiring to the defibrillator for the defibrillator to administer, via the electrodes a brief, strong electric pulse through the body of the person. The pulse also known as a defibrillation shock also goes through the heart, in an attempt to restart it, for saving the life of the person.

The defibrillation site may also be provided with an electrocardiogram (ECG) or other medical tool that is interfaced to the defibrillator processor module for providing the defibrillator processor module with patient parameter data for use by the defibrillator in controlling the defibrillation shock. For example, the ECG typically includes a set of electrodes adapted for monitoring the ECG of a patient. For example, in the standard 12 ECG lead system, the ECG leads are divided into limb leads, called—I, II, III, aVR, aVL and aVF—and precordial (chest) leads called—V1, V2, V3, V4, V5, V6. The ECG voltage potential between pairs of electrodes can be measured and recorded. The graphical display of these currents is known as an electrocardiogram, which is often referred to as an ECG. The ECG data may provide the defibrillator processor with valuable information for use in managing the defibrillation charge. For example, the ECG data may be displayed by the defibrillator processor on a display and is useful in revealing the condition of the heart and to diagnosis heart ailments or disease.

The defibrillator 410 comprises a defibrillator processor module 420, an energy storage device 442, a defibrillation port 414, a display 424, a user interface 440, and advantageously a decision support module 450 of this disclosure.

The energy storage device 442, the defibrillation port 414, and the user interface 550 have been previously described in FIG. 3 and that description is applicable to the description of these elements shown in FIG. 4. In an alternative embodiments, the defibrillator 410 may also include a parameter module 442, an ECG data feed module 443, other data feeds module 444, a loudspeaker 445, and a microphone 446.

The defibrillator processor 422 controls when an electrical charge is applied to a patient. The defibrillator processor 422 also controls other hardware and software residing in the defibrillator. The defibrillator processor may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The memory unit 422 can be any form of data storage device. It may be at least one of random access memory (RAM) and/or read only memory (ROM). Information can be stored permanently until overwritten and/or stored temporarily for use while the unit is active.

The display 424 may be a visual display capable of displaying data transmitted from defibrillator processor 435. Displays for use with this disclosure may include an LCD screen, an e-paper display, or other bi-stable display, a CRT display or any other type of visual display.

The parameter module 442 may be any monitor configured to detect a parameter of a patient. The patient parameter may include one or more of the following measurements: a measurement of $CO_2$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The patient parameter of the $CO_2$ exhaled by a patient may be measured using capnography techniques. The patient parameter of the electrical activity of the heart of a patient may be measured using ECG techniques. The patient parameter of the exchange of air between the lungs of a patient and the atmosphere may be measured using ventilation techniques. The patient parameter of the measurement of the pressure of the blood in a patient may be measured using non-invasive blood pressure measurement techniques or invasive blood pressure measurement techniques. The patient parameter of the temperature of a patient may be measured using temperature measurement techniques. The patient parameter of the oxygen saturation in the blood of a patient may be measured using pulse oximeter techniques or tissue oximetry techniques. The patient parameter of the chest compression of a patient may be measured using chest compression detection and feedback techniques. The patient parameter of the image of the internal structure of a patient may be measured using ultrasound measurement techniques. The patient parameter of the oxygen saturation in the blood in the brain of a patient may be measured using cerebral oximetry techniques. The patient parameter of the acidity or alkalinity of fluids in a patient may be measured using non-invasive pH measurement techniques. These and other techniques and modules for generating the foregoing and other kind of patient parameter data for use with this disclosure are well known in the art.

The ECG data feed module 443 is a module configured to manage the feed of ECG data from an electrocardiogram (ECG) that may be tethered to the defibrillator. The other data feeds module 444 is configured to manage the feed of other data from within or from outside the defibrillator. The loudspeaker 445 is a device for converting electrical signals representative of coaching information into audible information for use by a caregiver. The microphone 446 is a device for converting audible coaching information into electrical signals for use by the defibrillator.

Communication module 430 is hardware and software configured to transmit data to and from the defibrillator 410. Illustratively, the communication module 630 is configured to transmit data from the defibrillator to the external utility 415. The external utility 415 may be a computer, a laptop, a server, a mobile computing device, or other computing device. The external utility may also include a display screen for use as a display to monitor a patient. Alternatively, the defibrillator processor 420 may receive data from the external utility through the communication module 430 to the defibrillator 410. Hence, communication module 430 provides for the bidirectional transmission of data between the defibrillator 410 and the external utility 415. In order to allow for the bidirectional flow of data between the defibrillator and the external utility, the external utility is likewise provided with a communication module (not shown) that is compatible with the communication module 430 as required to establish the communication link with the communication module 430 of the defibrillator. Together, the communication module of the defibrillator and the external utility 415, respectively, enable a communication link 416 to be established between the defibrillator processor 420 and the external utility 415 for enabling the bidirectional flow of data between the defibrillator and external utility devices.

In an illustrative embodiment, the communication module 430 may include a wireless module 432 and/or a network data connect module 434 as shown in FIG. 4. The wireless module may illustratively be a Wi-Fi module. Alternatively, the wireless module 684 may be a blue tooth module, a CDMA module, or any other communication module that enables a wireless communication link for the bidirectional flow of data between devices wirelessly. The network data connect module 434 may be a hardware and software based data connector configured to connect with a data outlet of the external utility 416. The network data connect module 434 may be one or more ports and associated circuitry and software that allow bidirectional flow of data between the defibrillator processor 420 and the external utility 415. Illustratively, the network data connect module is an Ethernet connector configured for connection to the external utility 414 in a wired connection. Alternatively, the network data connect module may be an RS232 connector, a USB or other wire connector. Other connectors and hardware and software configurable for providing a wired connection between the communication module 430 and the external utility 415 may be used for network data connect module 434 as are well known in the art.

The decision support module 450 is hardware and software configured to advantageously enable work flows to be modeled as a graph of interdependent tasks to be performed. The decision support module 450 is described in detail below.

The external utility 415 is one or more programmed computers that may be connected to the defibrillator 410 wirelessly or by wired connection in order to allow for the exchange of information between the defibrillator and the external utility. The external utility of this disclosure may be a server. A server may be any computer configured to serve the requests of client programs running on the same or other computers on a network. In FIG. 4, the computer of the external utility may be a host computer configured to serve the requests of one or more client programs residing in the defibrillator 410. Alternatively, the computer of the external utility may serve a client residing on the external utility or on some other computer to which the external utility may be connected. Depending on the computing service that the server is configured to offer, the server may include one or more of a file server for storing and making files accessible for reading and writing to the client, a print server that manages one or more printers, a network server that manages network traffic, a mail server that manages mail on a network, a database server that allows clients to interact with a database, and/or a hospital server for managing hospital records. The server may also be in communication with one or more other servers that themselves may include one or more of the foregoing or other servers.

The external computing device may be a personal computer, a laptop computer, a tablet, a mobile computing device, or a server. The external utilities may include an adjunct medical device which may be a programmed computer that provides tools for monitoring the technique of a rescuer during the defibrillation process, such as applying CPR or proper positioning of the electrodes for application of a defibrillation charge on the patient. Illustratively, the device may monitor CPR chest compressions provided before or after defibrillation shock. For example, the device may measure the depth of a CPR chest compression, compare it to what it should be, and provide feedback to the user by way of instructions to go faster, deeper, etc. Alternatively, the adjunct medical device may be any other device that monitors defibrillation techniques and provides feedback to a rescuer at the site of the defibrillation.

Utility applications may also include existing applications that may be one or more software applications running on one or more computing devices external to the data processor module for performing a dedicated function. Examples of such functions include: performing specific services or tests.

Advantageously, the defibrillator of FIG. 4 is provided with the decision support module 450 of this disclosure. Alternatively, the decision support model may be provided to any medical device. The decision support module 450 comprises a task file module 470, a configuration files module 480, a data and model profile bank 462, a decision support event bank 464, a decision support protocol bank 466, a decision support manager module 490, and a dashboard generator 494.

As previously described, the decision support module 450 is hardware and software configured to advantageously enable work flows to be modeled as a graph of interdependent tasks to be performed. The decision support module illustratively comprises a task file module 470, a configuration files module 480, data and mode profile bank 462, decisions support event bank 464, decision support protocol bank 466, decision support manager module 490, and dashboard generator.

Figure 5:
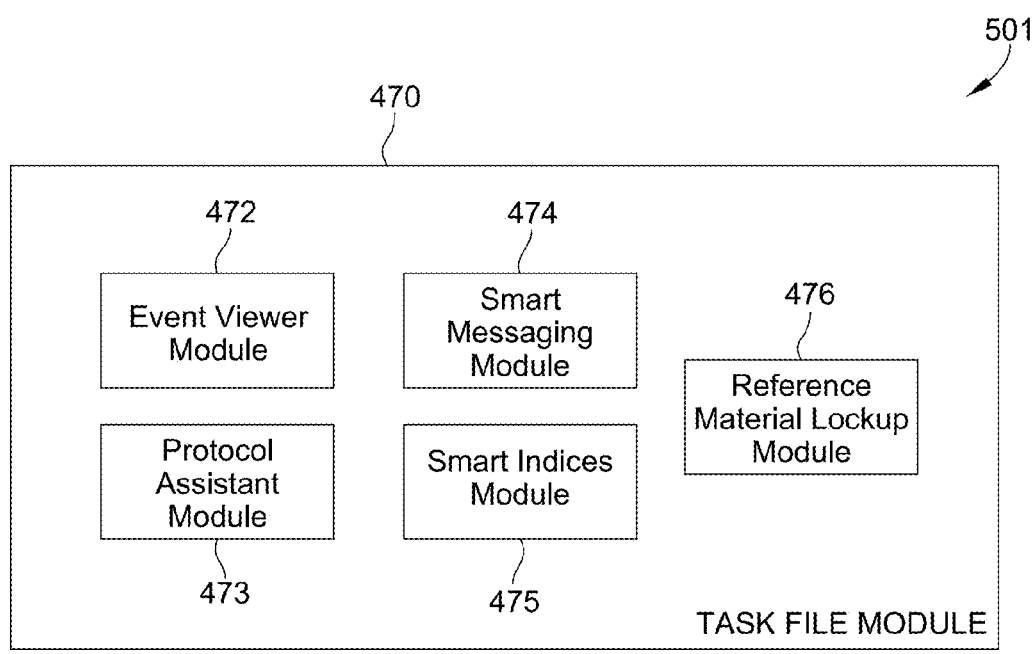
FIG. 5 is an enlarged view of the task file module included in the defibrillator of the defibrillator system in FIG. 4.

The task file module 470 is hardware and software configured to define the tasks to be performed by the decision support module 450 and to define and enable interactions between the tasks. As shown in FIG. 5, the task file module illustratively includes an event viewer module 472, a protocol assistant module 473, a smart messaging module 474, a smart indices module 475, and a reference material lookup module 476 for the purpose of defining the tasks and their independencies into a work flow. These modules and the functionality and the overall architecture of the decision support module is provided later in this description below.

The configuration files module 480 is hardware and software configured to specify a configuration for execution of one of the tasks residing in the task file module. The configuration files module 480 illustratively provides the configurations for the data and data flow for each task that is available to the task file module 470 for generating graphical interdependencies between the task files into one coherent work flow While the configuration files module 480 is illustrated in FIG. 4 as a module that is separate and apart from task file module 470, it will be appreciated to one skilled in the art to which this disclosure pertains that the configuration files module 480 may be integrated into the task file module 470 so that the task file module 470 defines both the configurations for the individual tasks as well as defining the interpedencies between those tasks into one coherent work flow.

The data and model profile bank 462 is hardware and software configured to store data and model profile constructs. The decision support event bank is hardware and software configured to provide events for the performance of tasks. The decision support protocol bank is hardware and software configured to provide protocols for the performance of tasks. The data and model profile bank, the decision support event bank, and the decision support protocol bank may be fed by a data feed from the parameter module 442, an ECG data feed from the ECG data feed module 443, a data feed from another data feeds module 444, a data feed entered through the user interface 440, a data feed from the external utility 415 by wire or wirelessly over the communication link 416, or a data feed provided by other sources. The data and model profile bank, the decision support event bank, and the decision support protocol bank may be fed in these and other ways from these data feed sources directly or indirectly through one or more of the other elements that make up the decision support module that have been directly feed data from these data feed sources. Hence, each element may illustratively provide a node for receiving data generated internally or externally of the defibrillator directly from a feed source or indirectly from any one or more elements that make up the decision support module that receives a data feed directly from a feed source, in a specific manner defined by the configuration of the decision support module. While the data and model profile bank, the decision support event bank, and the decision support protocol banks are shown in FIG. 4 separate and apart from each other, it will be appreciated to one skilled in the art to which this disclosure pertains that these banks may be integrated into one bank that is configured to provide data and model profiles, events, and protocols to the decision support module.

The data, events, and protocols may be used by the configuration module in configuring the tasks, by the task file module in defining interdependencies between tasks, and by the decision manager module and the dashboard generator in a manner described below. The data, events, and protocols in the data and model profile bank 462, the decision support event bank 464, and the decision support protocol bank 466 may be used by the decision support module to perform a current operation. The data, events, and protocols may also be used for operations designed for generating historic information or operation or for use for prospective purposes. The data, events, and protocols may generally be used for the purpose of enhancing the coaching of a user with respect to a medical procedure. Additionally, the data, events, and protocols may be used for other purposes, such as validating data in the data and model profile bank 462, the decision support event bank 464, and/or the decision support protocol bank 466.

The decision support manager module is hardware and software configured to to construct a dependency graph of the work flow of interdependent tasks defined by the task file module 470 using task configurations for each task provided by the configuration files module 480. The decision support manager module is further configured to execute the dependency graph.

Illustratively, the decision support manager module may further be configured as an engine for collecting, aggregating, and/or managing the data and model profile, the events, and the protocols from the data and model profile bank 462, the decision support event bank 464, and the decision support protocol bank 466, respectively, for use by the configuration files module 480 in configuring the task and by the task file module 470 in creating interdependencies between the tasks. Alternatively, this collection, aggregation, managing engine may be performed by the task file module 470 or the configuration files module 480 or distributed across one or more of the modules of the decision support module The dashboard generator is hardware and software configured to provide a display of the dependency graphs of the various workflow tasks of the work flow of interdependent tasks defined by the task file module 470 using task configurations for each task provided by the configuration files module 480. The dashboard may further configured to display other information such as decision points, decision reminders, possible etiologies, checklists, caregiver input, physiological data, trend line, timeline, time stamping, location, previous patient encounters, categories of data, timers that are set by data entry, etc. The dashboard may be further configured to display other information like check-off completions, predefined selections, care givers available, currently attending, or available, parameter or other information, coordination of data feeds from one or more inputs, defibrillator therapy activities, activities of partner systems, video procedures. For example, a video laryngoscope may provide tasks like apply the ventilator, check the heart rate, preview patient data. Configuration settings may be displayed such as user level, patient condition, the condition of the patient. The condition of the patient may be presented by display of patient data such as EMR, ePERS, and EMS. The tasks may display historic patient parameter profiles for the patient for comparison with current patient parameter profile. The tasks may display patient parameter profiles for a health patient for comparison with the parameter profile of the current patient.

Figure 6:
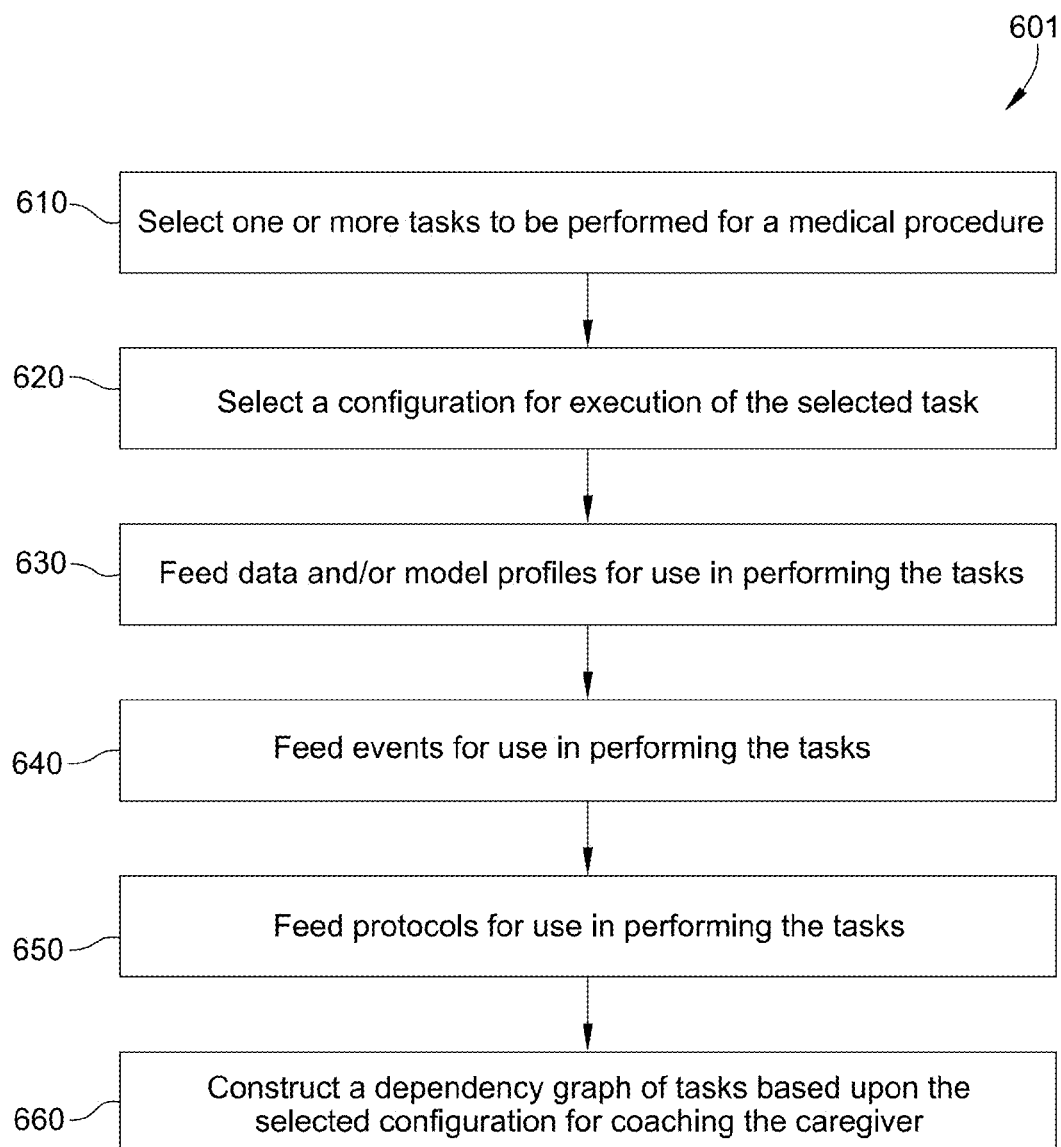
FIG. 6 is a flowchart for the modeling of a graph of interdependent tasks to be performed for a medical procedure.

The operation of the decision support module 410 of FIG. 4 is illustratively shown in FIG. 6 as a flowchart for the modeling of a graph of interdependent tasks to be performed for a medical procedure. As illustrated, the operation begins by selecting 610 one or more tasks to be performed for a medical procedure. The selection may be made through the user interface 440 by user activation of a manual key. Alternatively, the selection may be made from a remote location by the external utility 415. In another illustrative example, the selection may be triggered by instructions residing in one or more of the elements residing in the decision support module.

The decision support module selects 620 a configuration for execution of the selected one or more task. Data and/or model profile feed 630, events feed 640, and/or protocols feed 650 is collected and aggregated by the decision support manager module for correlations performed by the configuration files in correlating the configurations for the one or more tasks and for correlations performed by the task file module in correlating interdependencies between the one or more tasks by the task file module and by the decision support manger module in correlating the graphing of the workflow of interdependencies between the one or more tasks defined by the task file module using the configurations for the one or more tasks defined by the configuration files module. Finally, the decision support module constructs 660 the dependency graph of tasks based upon the selected configuration for coaching the caregiver.

In a further operation, the dashboard generator 494 provides the display of the dependency graphs of the various workflow tasks of the work flow of interdependent tasks defined by the task file module 470 using task configurations for each task provided by the configuration files module 480.

Figure 7:
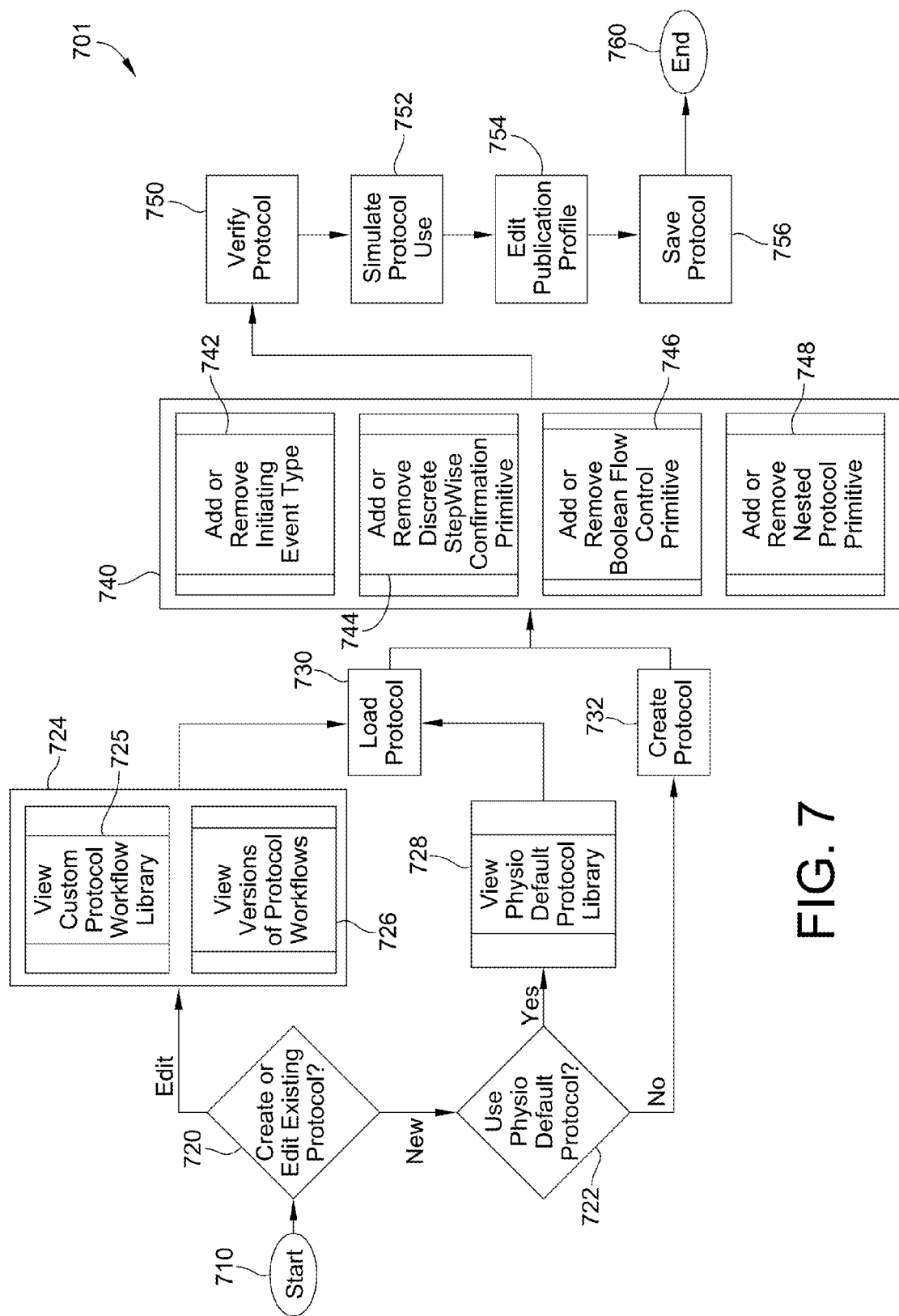
FIG. 7 is a flow chart for the creation of a workflow according to this disclosure.

FIG. 7 illustrates a workflow creation module 701 of hardware and software configured for the creation of a workflow according to this disclosure. The module resides on a computer which illustratively is a computer that is an external utility.

Illustratively, the workflow creation module 701 of this disclosure serves as an editor advantageously for the creation of the workflow for the medical devices, such as defibrillators. In other words, the workflow creation module may provide the editor for configuring the configuration of the decision support module of the medical device; illustratively providing configurations for the configuration files in the configuration file module of the decision support module on the medical device. For example, the workflow creation module may define the protocols that the decision support module is to follow in managing the clinical display on the medical device. The workflow creation module may further configure clinical data residing on servers that may be accessed by the medical device with protocols, rules, etc. for delivery and display to the decision support module according to this disclosure.

The editing by the external utility thus provides one decision support logic that may be shared with a medical device, such as a defibrillator. In addition, the external utility may provide other decision support logic and decision support information to the medical device. For example, as previously explained, the external utility of this disclosure may be a server configured to serve the requests of client programs running on the medical device. Depending on the computing service that the external utility configured as a server may offer, the external utility may include files, data, references, data and other decision support information that the external utility may share with the defibrillator or other medical device.

Illustratively, the computer that includes a workflow creation module 701 is an ITablet although any computer may be used. Alternatively, the module may reside on the defibrillator itself. Advantageously, the location of the workflow creation module 701 in an external utility enables the workflow created by the workflow creation module to be distributed to one or more defibrillators in the network over communication link 415. However, it will be appreciated that any one defibrillator provides a network terminal on the network and so may be used for the creation and source of distribution of workflow to defibrillators throughout the network.

As shown in FIG. 7, the workflow creation begins at start 710. An option 720 to create or edit an existing protocol allows a user to edit 724 an existing protocol or create 722 a new protocol. An edit 724 of an existing protocol allows the user to view a library 725 of custom protocol workflows and to view versions 726 of protocol workflows for selection 730 for loading as the workflow to use in the instant workflow process being defined by the workflow creation module 730.

The create 722 new protocol allows a user to either create a protocol by either a view 728 of a default protocol library or create 732 of a protocol. The selection 730 of either view 728 or create 732 options loads the selected protocol as the workflow to use in the instant workflow process being defined by the workflow creation module 730.

An editor 740 allows a user to add or remove an initiating event 742, a discrete stepwise confirmation primitive 744, a Boolean flow control primitive 746, and/or a nested protocol primitive 748. The initiating event 742 is an event that may be used to trigger the deployment of an interdependent task on the occurrence of the event. The discrete stepwise confirmation primitive is the smallest 'unit of processing' available to a programmer of the particular machine used to impalement the workflow or an atomic element of an expression in a language for confirming the occurrence of an event. The Boolean flow control primitive is a primitive of Boolean operations that define the flow of the protocol. The nested protocol primitive is a primitive used to nest one or more protocols within one or more protocols.

The protocol configured by the editor 740 is verified 750, simulated 752, and the publication profile is edited 754. The protocol so configured is saved 756 and the creation of the workflow is ended 760.

Figure 8:
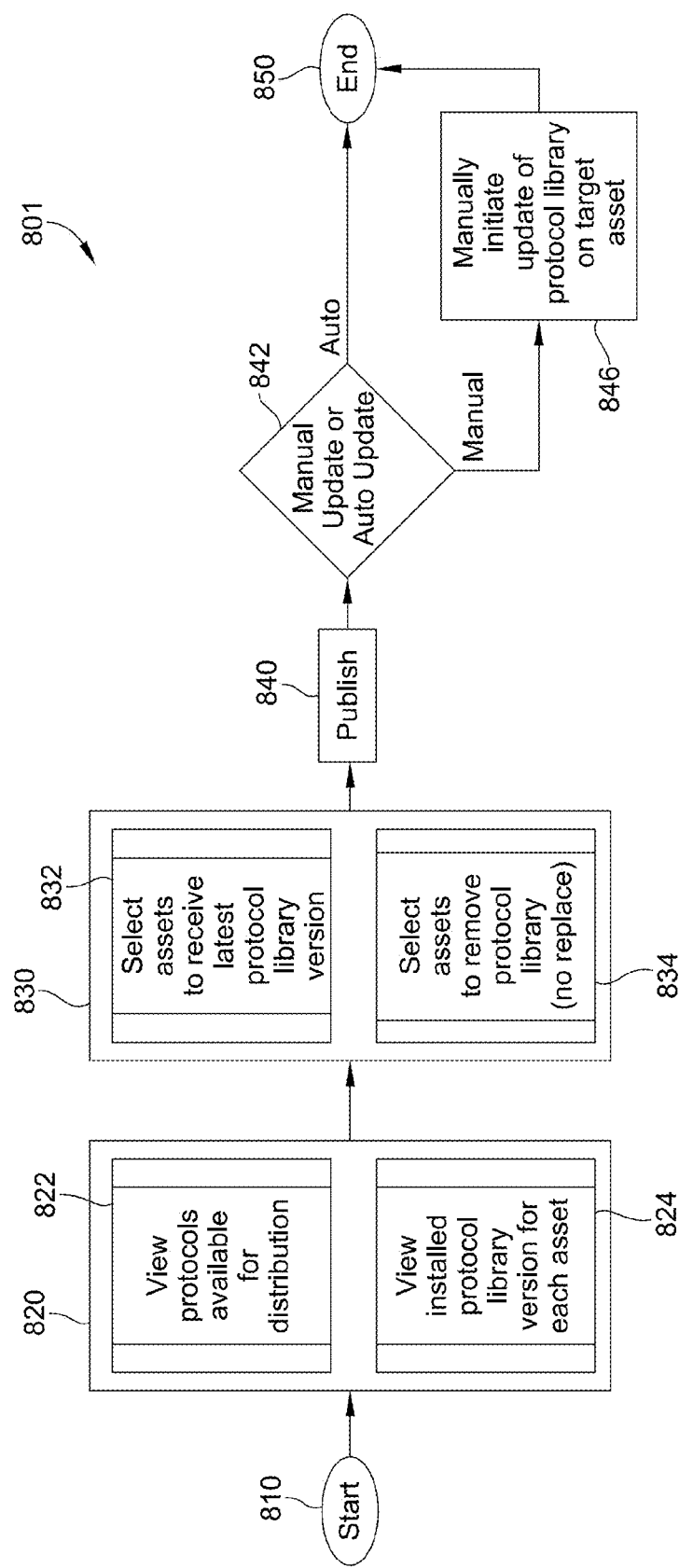
FIG. 8 is a flow chart for distributing a workflow according to this disclosure.

FIG. 8 illustrates a workflow distribution module 801 of hardware and software configured for the distribution of a workflow according to this disclosure. The module resides on a computer which illustratively is a computer that is an external utility; but as previously described in connection with the workflow creation module, the workflow distribution module may reside on the defibrillator itself.

As shown in FIG. 8, the workflow distribution begins at start 810. An option 820 allows a user to view 822 available for distribution and/or to view 824 an installed protocol library version for each asset, which is each terminal on the network that is to receive the created workflow. The terminal is illustratively a defibrillator but may be any medical device for providing coaching of a user during a medical procedure. An option 830 allows a user to select 832 assets to receive latest protocol library version and/or to select assets to remove protocol library with no replacement of the protocol and the workflow is published to the asset. The published workflow includes a manual or auto update feature 842. If the setting is manual, the asset is enabled to update the protocol library upon manual activation of a button or other active link on the asset. If the setting is automatic, the asset is enabled to perform the update automatically by the network. The workflow distribution enablement of an asset is thus completed at end 850. Actual configuration of the asset with the distributed workflow occurs on the automatic update of the configuration settings of the workflow of the asset by the network or upon the manual activation of a button on the asset by a user.

Figure 9:
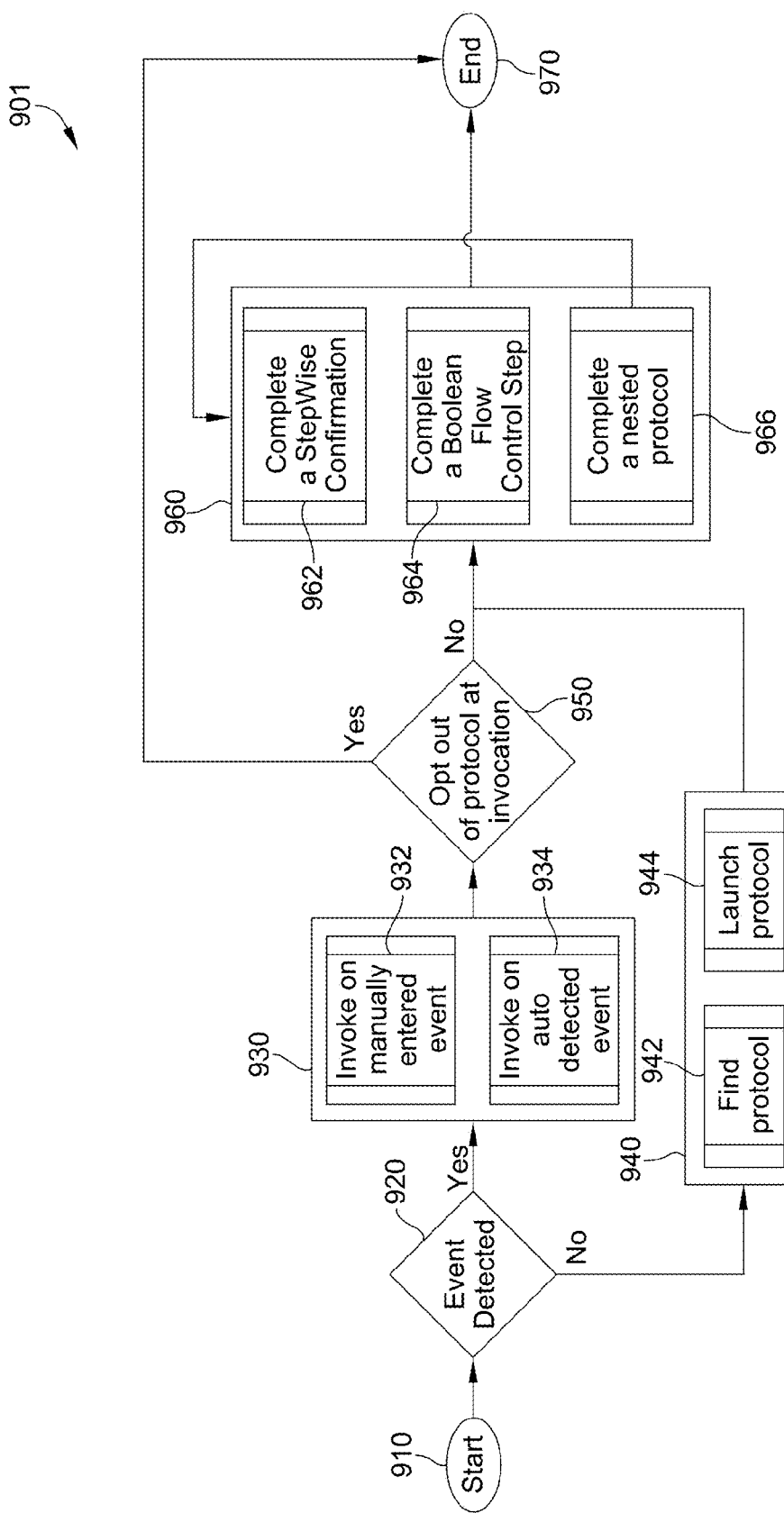
FIG. 9 is a flow chart for the execution of a workflow according to this disclosure.

FIG. 9 illustrates a workflow execution module 901 of hardware and software configured for the execution of a workflow according to this disclosure. The module resides in a computer which illustratively is a computer that is the asset making use of the module, such as a defibrillator.

However, as previously described, the module may reside on an external utility with the output of the data feed generated by the workflow execution module fed to the defibrillator over communication line 416.

As shown in FIG. 9, the workflow execution begins at start 910. A detector 920 of an event allows detection by the workflow execution monitor of an event. An invocation 930 allows the workflow execution monitor to invoke the event manually 932 or upon automatic detection 934. The opt out 950 allows the workflow execution monitor to opt out of invoking the protocol. On opt out, the workflow execution ends 970. If the workflow execution monitor does not opt out, a completion module 960 allows the workflow execution monitor to complete a stepwise confirmation on the invoked event 962, completion of a set of Boolean flow control operations 964 that define the flow of the protocol, and completion of a nested protocol 966 to that nests one or more protocols within one or more protocols. The workflow module 960 then ends 970.

In the event the event detector 920 detects no event, the workflow execution module 901 advances to a protocol module 940 to find an applicable protocol 942 and launch the protocol 944. After the protocol is launched, the workflow execution module advances to the completion module 960 where the workflow execution monitor is allowed to complete a stepwise confirmation on the invoked event 962, completion of a set of Boolean flow control operations 964 that define the flow of the protocol, and completion of a nested protocol 966 to that nests one or more protocols within one or more protocols. The workflow module 960 then ends 970.

Referring again to FIG. 5, more details of the task file module 470 will now be provided. As shown in FIG. 5, the task file module illustratively includes the event viewer module 472, the protocol assistant module 473, the smart messaging module 474, the smart indices module 475, and the reference material lookup module 476 for the purpose of defining the tasks and their independencies into a work flow. In all of these modules, the decision support manager module allows the user to create pre-defined messaging that will be available. Each message will have some form of an input to trigger the message. The input may be an initiating event or it may be a timed based Boolean equation using a combination of Vital Sign data and events. Each message will also have some form of output. The output may be no output displayed because the normal output may no longer be necessary, such as for example, because other events have occurred that have preempted the need to display that message. The output may be tied to a standard set of events or a user pre-defined hierarchy of manually enterable events described above.

Figure 10:
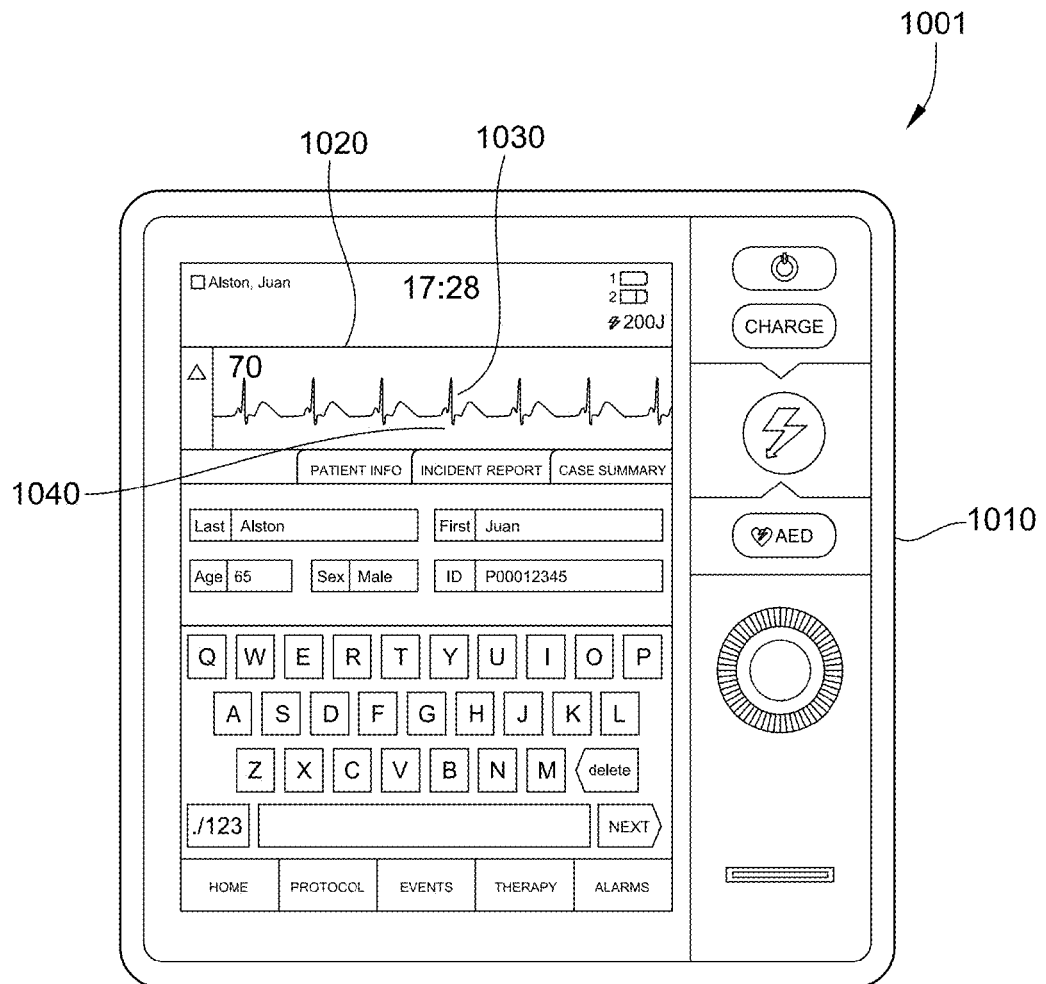
FIGS. 10-18 show a defibrillator of the defibrillator system of FIG. 4 displaying illustrative screen shots according to this disclosure.

The event viewer module 472 is a software and hardware configuration of a construct for generating a series of timed stamp events so that the user can see what has happened with this patient. An event may be any individual data point or groupings of data points. Illustratively, an event is a grouping of data points which may be displayed on the display of the defibrillator. For example, FIG. 10 shows a defibrillator 1010 of a defibrillator system 1001 displaying illustrative screen shot 1020 according to this disclosure. Illustratively, screen shot 1020 depicts a workflow 1030 in this example as a non-indexed view of the major vitals signs as they vary over time. The event in this example may be referred to as the "Sparkline" view. Sparklines can be defaulted to show up on the screen at startup, such as to provide a waveform along a bottom region of the display. The spark line can be selected to be displayed in any of the regions of the display at any time. Alternatively, a user may select when to display a sparkline. For example, an event button may be provided for the user to activate to display the "pre-defined hierarchy of manually enterable events. The user may activate the event button to bring up the Sparkline view at predetermined or any period of time.

The Sparkline view illustratively includes one or more event markers 1040 shown on the Sparkline by the inverted triangle appearing at the bottom of each spike depicted in the Sparkline. Hence, in this example, the Sparkline includes a series of event markers running along the bottom of the Sparkline with each event marker associated with a spike depicted by in the Sparkline. More specifically, in the decision support module of this disclosure, the dashboard generator module generates the Sparkline non-indexed view of the major vital sign as it varies over time. The event viewer module provides the event marker at a point in time along the non-indexed view of the major vital sign. The event marker provides a record of one or more predetermined events associated with the major sign at that point in time. In other words, the event marker shows where the defibrillator has captured events at that point in time.

The event marker may be used by the user to do a variety of tasks. For example, the event marker allows a user to zoom in on a specific vital sign, that is to say, to an indexed view. The event marker may allow a user to zoom in on a specific time period. In other words, the user may use the event marker to narrow the period and widen the view of the Sparkline. The event marker may allow a user to zoom in on a specific event; in other words, to view the event details including captured waveforms. The event marker may allow a user to add an event, such as by pulling up a "user pre-defined hierarchy of manually enterable events to add to the event record. The event marker may be used to change the view to a list view of time stamped events. The event marker may be used to expand the view to cover two waveform regions instead of one. The event marker may allow the user to navigate back to the Sparkline view.

While FIG. 10 shows the generation of a Sparkline by the decision support manager module, it will be appreciated that the decision support manager module may generate work flows for other vital signs. The vital sign may include time changing data on heart beat, SpO2, CO2, temperature, an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The events in the record that is represented by the event marker may be one or more predetermined events including an indexed view of the vital sign, a view of the vital sign over a specific period of time, a specific event, details of a specific event, a time stamped event, a listing of time stamped events, a view of one or more different vital signs at that point in time, a protocol, and so on. The events may also be a combination of one or more of the foregoing and other predetermined events.

The user may configure the event viewer module with the one or more events to be contained in the records that the event viewer module may associate with an event.

The event viewer module may provide a user with a hierarchy of manually programmable events. The hierarchy of manually programmable events may enable the user to define the one or more new events for configuring the record of the event marker.

The event viewer module provides an active forward link of the event marker to the records such that on user activation of the event marker, the forward link takes the user to the records that are associated with the event marker. In addition, the event viewer module provides an active reverse link of the event marker to the records such that on user activation of the active reverse link, the active reverse link takes the user from the records that are associated with the event marker back to the event marker.

The decision support manager module allows the user to create their custom set of user pre-defined hierarchy of manually enterable events. The names of these events may be defined by the user in their native language; thereby obviating the need for translations. The user may have the ability to determine what type of waveform storage goes with any event. For example, a user may define a waveform to be displayed for 8 seconds before occurrence of a subsequent event, 8 seconds after activation of an event marker, 4 seconds after activation of an event marker and before occurrence of a subsequent event. Alternatively, the user may configure the event marker to display no waveforms on the activation of an event marker.

Figure 11:
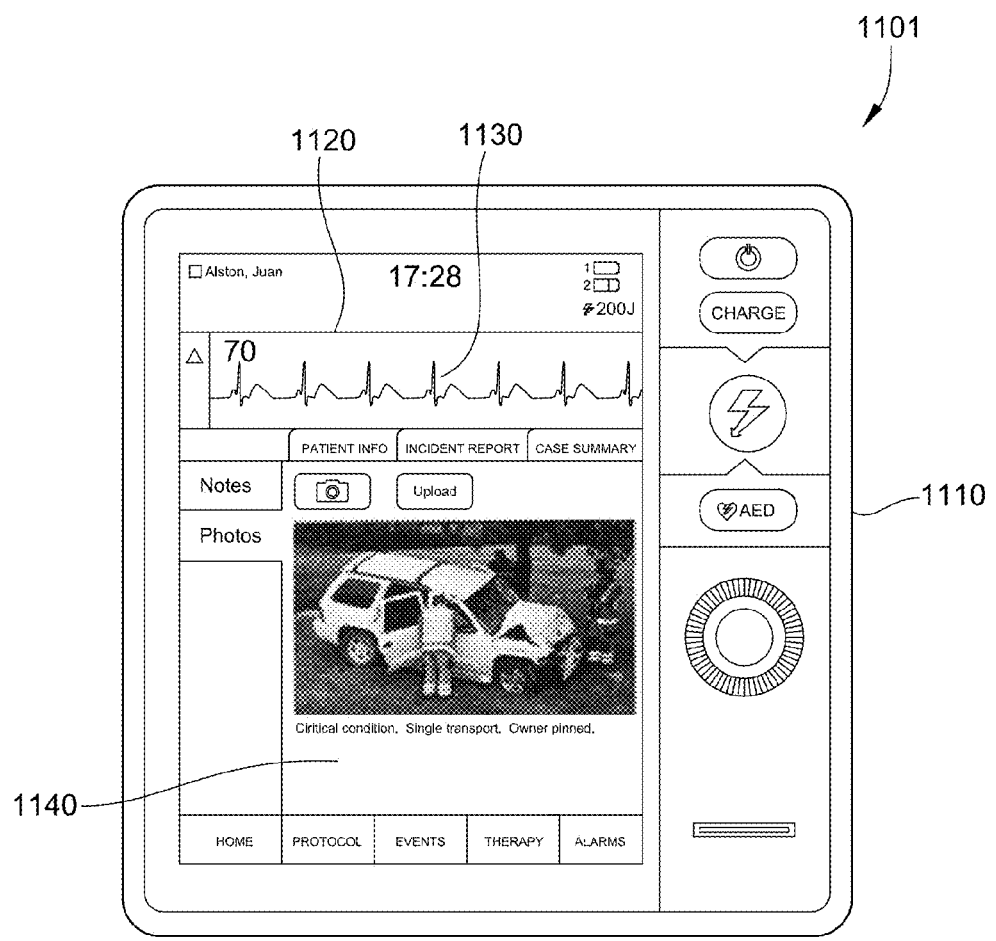

FIG. 11 shows a defibrillator 1110 of a defibrillator system 1101 displaying illustrative screen shot 1120 illustrating a workflow 1130 depicting an event 1140. The event 1140 was triggered by user activation of the event marker appearing as an inverted triangle at the bottom of the highlighted spiked signal in the workflow which contains an active forward link to the event 1040 in this example in accordance with this disclosure. In this example, the event 1140 is a picture of a vehicular accident along with a record appearing underneath the picture of some data that may be useful to a caregiver such as a description of the accident (e.g., frontal collision), description of the patients, description of the injuries, etc.

Figure 12:
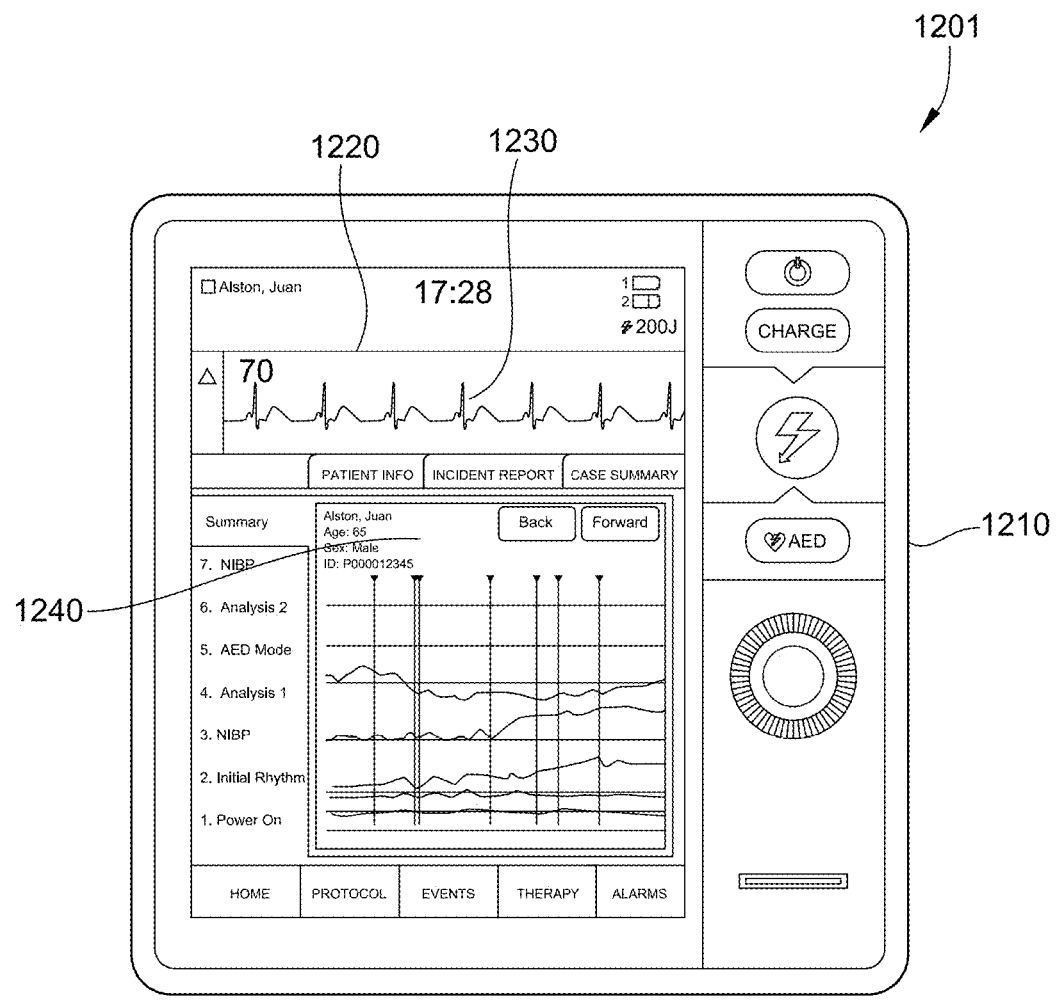

FIG. 12 shows a defibrillator 1210 of a defibrillator system 1201 displaying illustrative screen shot 1220 illustrating a workflow 1230 depicting an event 1240. In this example, the event displayed is a series of vital signs on one of the subjects involved in the vehicular accident shown in FIG. 11.

Figure 13:
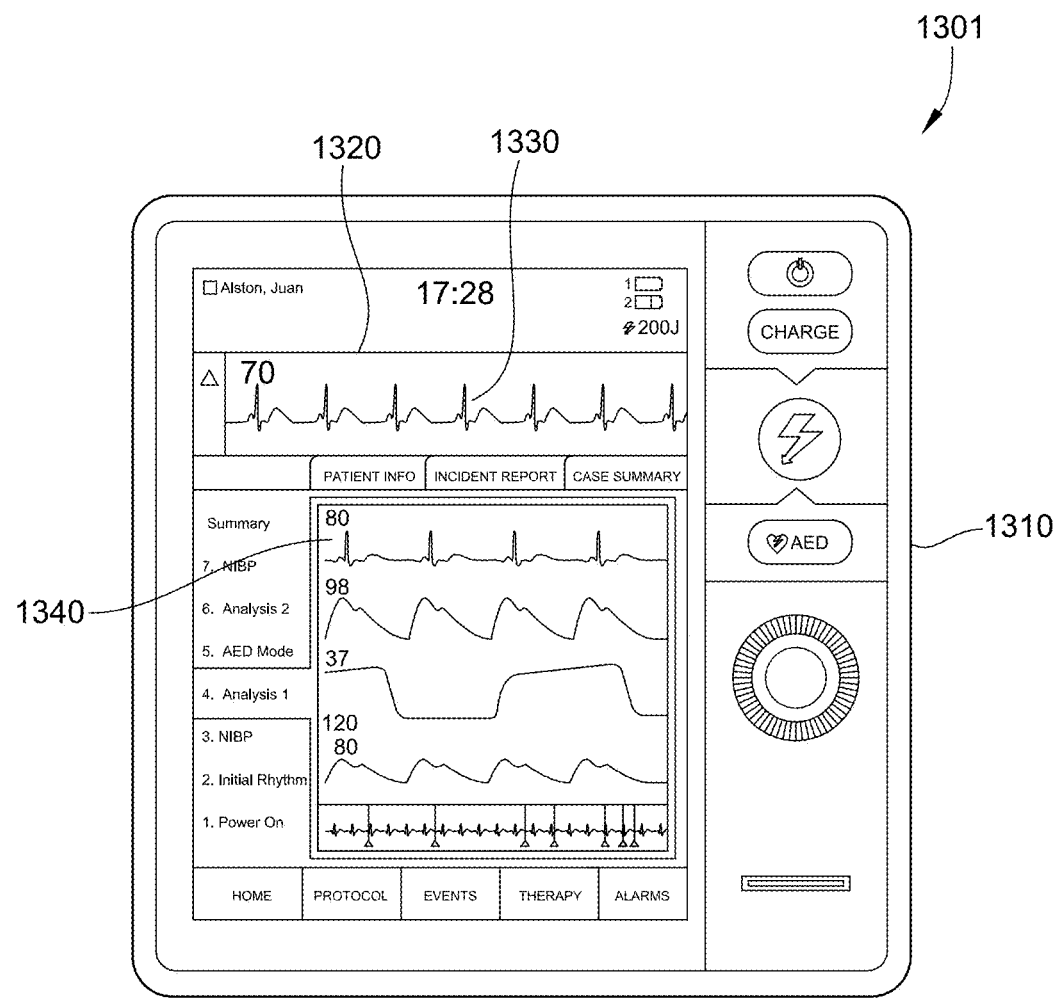

FIG. 13 shows a defibrillator 1310 of a defibrillator system 1301 displaying illustrative screen shot 1320 illustrating a workflow 1330 depicting an event 1340. In this example, the event displayed is a series of vital signs shown with additional patient parameter or other data on one of the subjects involved in the vehicular accident shown in FIG. 11

The event viewer module 472 of FIG. 5 may generate a time stamping on one or more of the events that the event viewer module may include in a record to be associated with an event marker. For example, each of the events illustrated in FIGS. 10-13 may be provided with a time stamp to indicate the time that the data in the record displayed on activation of the event marker occurred. In addition, the listing of data in the record associated with an event marker may be an active listing to which additional data may be added in real or batch time. Any one or more of the original or additional data may be time stamped to indicate to a caregiver the time at which the data is captured. Thus, the series of time stamped events generated by the event viewer module enables a caregiver to track what has happened with the patient.

The protocol assist module 473 shown in FIG. 4 is a software and hardware configuration of a construct for generating a pre-defined protocol of one or more activities that can be displayed with each activity of the one or more activities being checked off by a user when the each activity is completed. The protocol assistant module allows a user to display and acknowledge a series of user pre-defined actions, The protocol assistant module may be selected by manual activation of a protocol coach button 1410 appearing in a toolbar appearing at the top of the display shot. The protocol assistant module selection may also occur automatically on a display when certain events occur. For example, if data on a patient indicates chest pain, that data event may trigger the display of the protocol for the caregiver to follow in treating the patient.

Figure 14:
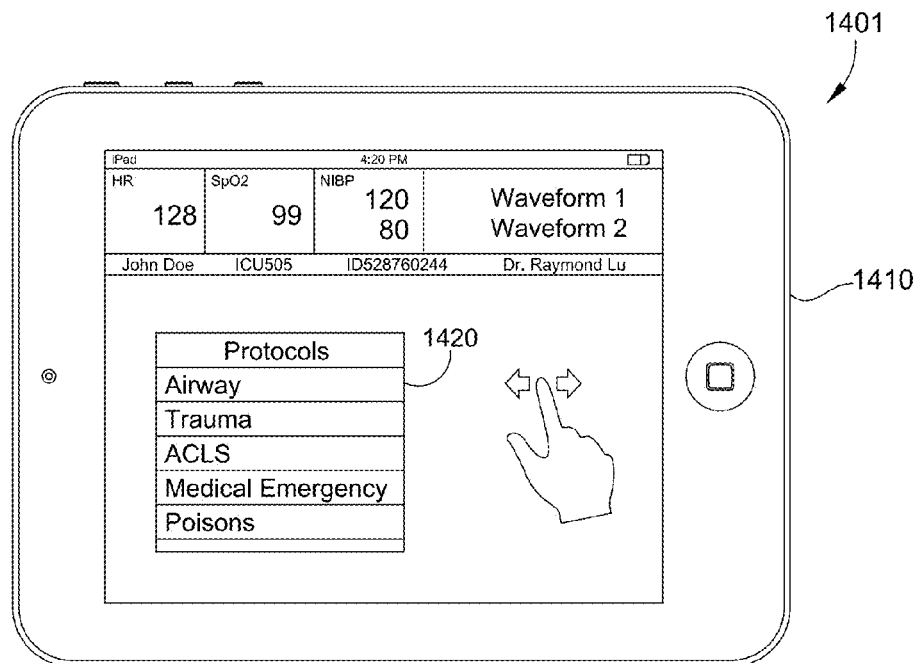

FIG. 14. shows a defibrillator 1410 of a defibrillator system 1401 displaying illustrative screen shot 1420 illustrating a listing of protocols that may be generated by the protocol assist module 473. The protocols generated by the protocol module in this illustrative example includes a protocol for treatment procedures for arising from an airway, a trauma, an advanced cardiac life support (ACLS), a medical emergency, and poisons.

Figure 15:
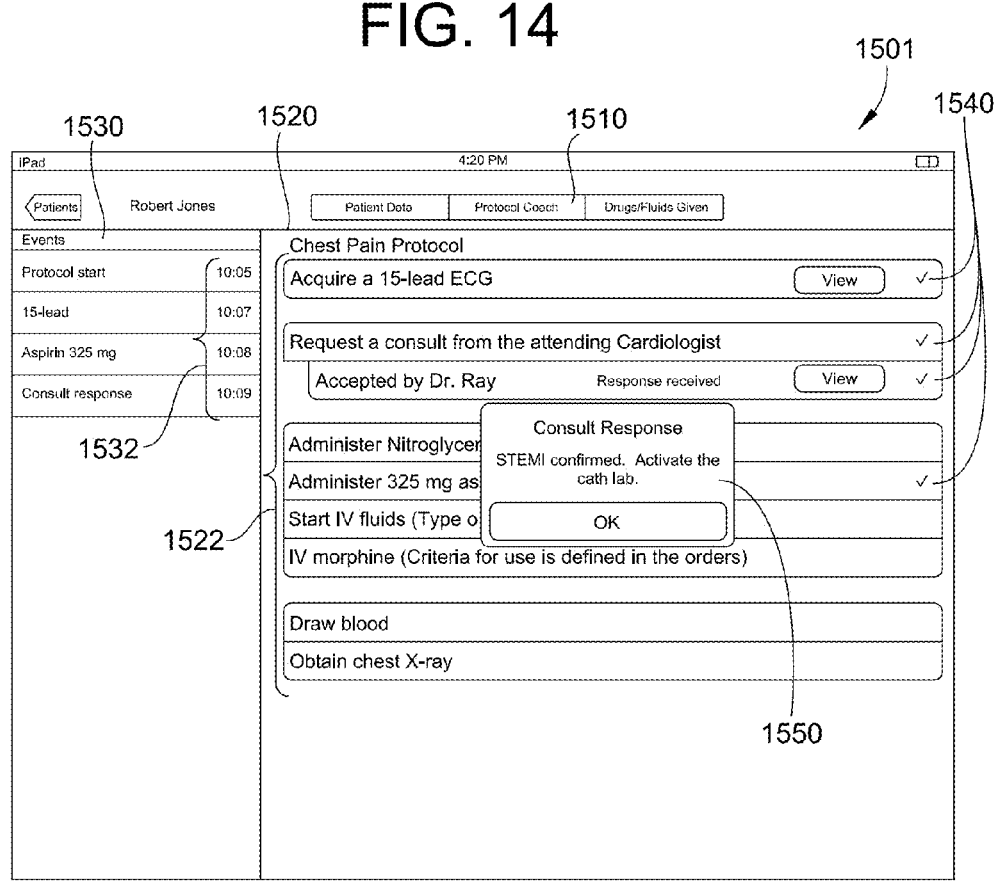

FIG. 15 shows a display of a chest pain protocol generated by the protocol assist module. More particularly, defibrillator 1510 of a defibrillator system 1501 displaying illustrative screen shot 1520 illustrating a workflow 1530 depicting an event 1540. In this example, the event displayed is a chest pain protocol. The user may select this protocol if a patient being treated is exhibiting chest pains. The screen shot 1520 displays this protocol as a series of steps 1522 for the caregiver to follow in order to treat the chest pains. The steps include acquiring a 15-lead ECG, consulting a cardiologist, administering certain medications, drawing blood, and obtaining a chest X-ray. The screen shot in this example may be a touch screen and each action may be associated with an active touch screen link. This allows a user to indicate completion of each task by touching the displayed task on the touch screen which causes a check-mark 1540 to be displayed next to each task showing which tasks have been completed. This feature allows a caregiver to monitor the tasks being completed by the caregiver as the caregiver performs each task in order to ensure that all of the tasks recommended by the selected procedure are completed and that they are performed in their recommended sequence.

The step in the protocol of requesting a consultation with a particular cardiologist allows the caregiver to interact on the spot with a medical specialist, in this case a Dr. Ray. The caregiver may accept the consultation by touching the consult response link 1550 on the screen shot. Once accepted, the caregiver will be brought into communication with the caregiver for the purpose of participating with the caregiver in the treatment of the patient. The communication link established between Dr. Ray and the caregiver may be by way of instant messaging, audio link, audio-video link, or in other ways.

The time stamping feature of this disclosure is shown in FIG. 15 in screen shot 1530 which shows events that are being tracked and displayed by the defibrillator 1510. In this example, the screen shot 1530 displays the events that make-up the chest pain protocol displayed in screen shot 1520. As previously described, screen shot 1520 shows each event as an active link for the caregiver to interact with for various purposes, such as check-marking the completion of a task, establishing a communication link with a consultant, etc. Screen shot 1530 shows these events in a running listing in which each event is added to the list once the caregiver has completed the event. Advantageously, the running listing also generates a time stamp 1532 for each event added to the running list so that the result is a running listing of a series of time stamped events for use in tracking what has happened with the patient.

In alternative embodiments, the one or more activities of the protocol may be displayed in a primary work area of a display unless information that is displayed in the primary work area of the display at the time the protocol is to be displayed is clinically critical information. The protocol assistant module may be configured to access the Sparkline non-indexed view of a major vital sign as it varies over time and to access an event marker at a point in time along the non-indexed view of the major vital sign generated by the event viewer module and to access a record of one or more predetermined events associated with the major sign at that point in time provided by the event marker. The protocol assistant module may be selected automatically on a display when certain events occur. The protocol assistant module may be selected manually using a protocol key. The protocol assistant module may include a user defined hierarchy of manually programmable protocols, the hierarchy of manually programmable protocols providing one or more protocols selectable by the user for configuring the protocol generated by the decision support module. The protocol assistant module may include a system defined hierarchy of manually programmable protocols, the hierarchy of manually programmable protocols providing one or more protocols selectable by the user for configuring the protocol generated by the decision support module.

The protocol assistant module thus provides a set of user pre-defined activities, that is to say, protocol, that can be displayed on the screen and have the user check off when they complete the activity. Each check-off would be timed stamped, and if the user pre-defined the activity to be associated with an event, an event would be automatically generated at the time of check-off. The protocol may appear in a primary work area of the screen such as along the bottom of a waveform region. When the protocol comes up, the information that was displayed in the primary work area may illustratively be moved to the background, unless it's currently displaying clinically critical information (e.g. AED Mode). From the protocol assistant module, a user can also pull up the Sparkline view as a part of the window to see events and checklist items in the same view area Protocols can be manually selected via a protocol key, or can appear on the screen automatically when certain events occur. Protocols may be created and organized (hierarchy for manual selection) by the user. The user may define whether the protocol is manually initiated, automatically initiated, or both. Automatic initiation may be connected to an event, so that when the event occurs, the protocol appears. Events can be the standard pre-defined events provided by the decision support module or by user specified events, such as from the pre-defined hierarchy of manually enterable events previously described. For each activity in the Protocol, the user can determine if a timed stamp Event is created at the time of selection or not.

The decision support management module will allow the user to create the protocols, and connect the protocol initiation events and to outputs. The output from the protocol may be no output if, for example, a protocol output is preempted because, for example, the decision support module may have determined that the protocol is no longer needed. The output may be tied to a standard set of events or to the user pre-defined hierarchy of manually enterable events described above.

Figure 16:
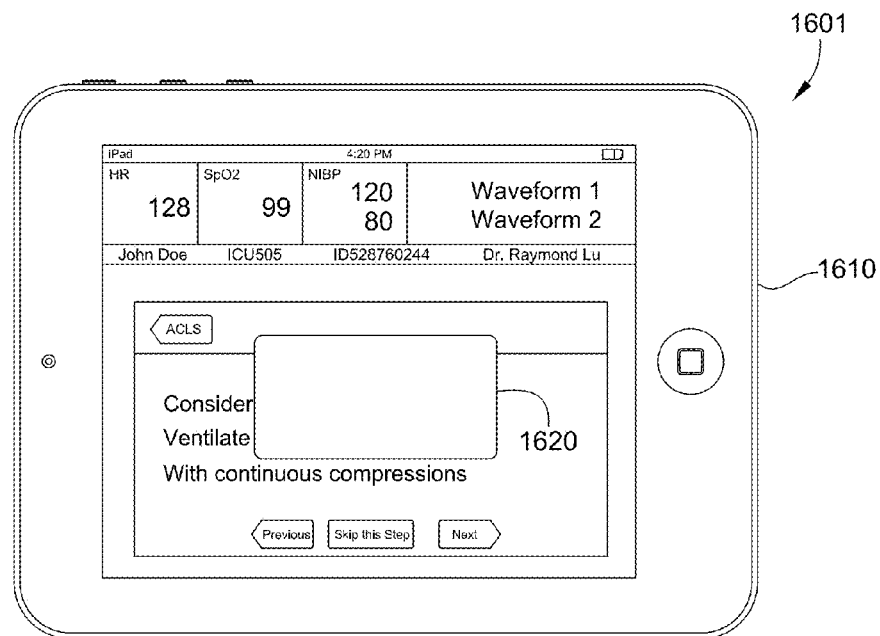

FIG. 16 shows a display of a smart message generated by the smart messaging module 474 shown in FIG. 4. The smart message module is a software and hardware configuration of a construct for generating smart messaging. As shown more particularly in FIG. 16, defibrillator 1610 of a defibrillator system 1601 displaying illustrative screen shot 1620 illustrating a pre-defined message. The pre-defined message may be displayed when an event has occurred and may continue being displayed until another event has occurred. In the illustrative example, the message is an instruction to the caregiver to administer a specified dosage of epinephrine. The display of the message may be triggered by an event such as an action in a protocol generated by the protocol assistant module. Alternatively, the display may be triggered by a parametric condition detected by the defibrillator such as data generated by the patient parameter module indicating a condition of the patient requiring the administration of this medication. The message could be in the in the form of an immediate action, a reminder to give more medication, an instruction to provide this medication within a specified period of time, a suggestion to consider calling a specialist such as a member of a rapid response team (RRT team), etc.

The messages may appear as pop-ups on the screen, overriding a portion of the general work area of the screen, such as along a bottom of a region of a waveform such as the sparkline. The caregiver illustratively has the ability to acknowledge or cancel the message, and the decision support module illustratively records that action. The acknowledgements is associated with an event that is automatically generated at the time of the acknowledgement. The caregiver may pre-define whether the acknowledgement of the message creates an event or not.

The action informed by the user message may be taken from the group of action consisting of a reminder, a reminder to take a medication, and a suggestion to contact one or more persons. The smart messaging module may include an input to the predefined message including an initiating event or a time based Boolean Equation using a combination of vital sign data and events. The output of a predefined message is a no output or an output tied to a standard set of events or an output based on a user predefined hierarchy of manually enterable events.

Figure 17:
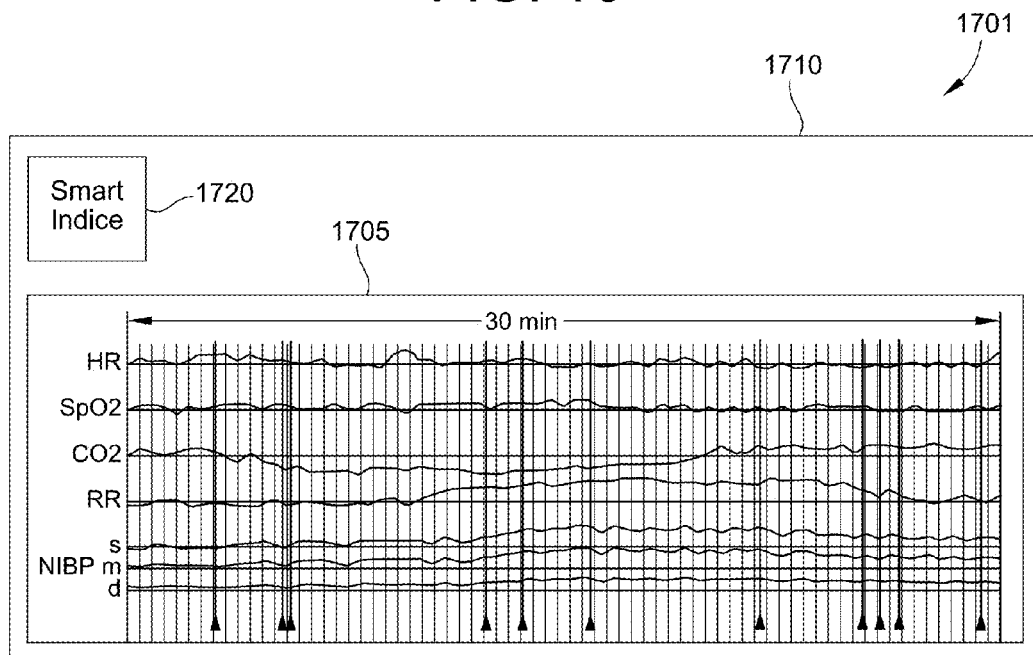

FIG. 17 shows a display of smart indices generated by the smart indices module 475 shown in FIG. 4. The smart indices module is a software and hardware configuration of a construct for generating a predefined indice value associated with the overall health of the patient. As shown more particularly in FIG. 17, defibrillator 1710 of a defibrillator system 1701 displaying illustrative screen shot 1720 of the smart indices. The smart indices appears above a display of one or more vital waveforms. However, it will be appreciated that the smart indices window may appear anywhere on the display of the defibrillator. The indice value appears as a vital sign information on a display and may be determined by a predefined indices algorithm. The indice value represents a health score for a patient and various indice values may be generated depending upon what set of patient parameters a caregiver may want included in the indice value. For example, an indice value that is configured to provide a health score on blood pressure may be configured to display an indice value for the blood pressure of the patient illustratively based upon the height and weight and other physical properties of the patient. As another example, an indice value may combine blood pressure and respiratory rate readings into a combined health score of the patient in which case each reading would be weighted in the health score rating according to the algorithm. Once selected the indice value may appear throughout a patient episode. The indice value may be programmed to appear at the beginning of each patient episode, manually selectable via a indices menu, or automatically displayed by initiating an event.

The decision support manager module allows the user to decide which preprogrammed indices are going to be used (OBS, IPI, etc.) and which customer defined ones will be available. For each selected indices, the user can define whether its configured to be there all of the time, manually selectable, or automatically initiated (via an Initiating Event)

Figure 18:
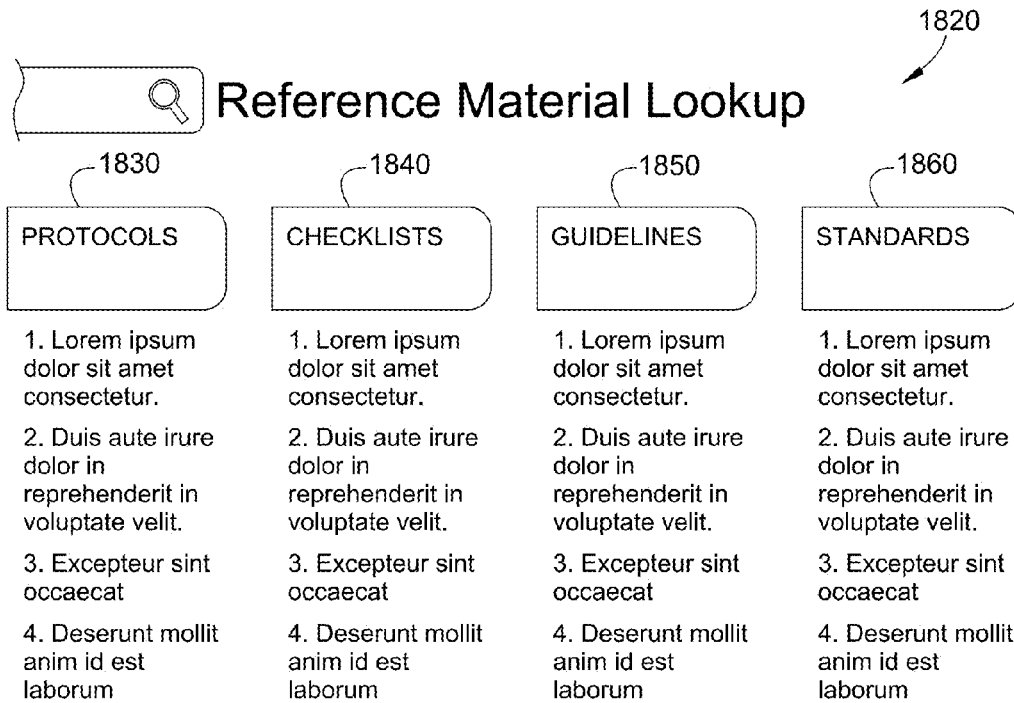

FIG. 18 shows a display of the reference material lookup display generated by the reference material lookup module 476 shown in FIG. 4. The reference material lookup module is a software and hardware configuration of a construct for generating a user pre-defined set of text and graphical information in some standard form (.pdf, .doc. html5). As shown more particularly in FIG. 18, defibrillator 1810 of a defibrillator system 1801 displaying illustrative screen shot 1820. The screen shot may illustratively display protocols 1830, checklists 1840, guidelines 1850, standards 1860. The screen shot may also display news, video, photos, tweets, other reference material, etc. The screen shot may display other modules of data and information such as a library module (not shown) of reference material of text and graphical information in some standard form (.pdf, .doc. html5). The reference material lookup module may be accessed manually via a user defined hierarchical menu of reference material. Alternatively, the reference material lookup module may be requested manually or automatically when reference material is associated with a protocol task of a smart message delivered by the decision support manager module. When the user requests the information, the pre-programmed information may be shown on the screen in a general work area such as below a region of a displayed waveform. The user may scroll up and down the information and close the menu when completed.

The decision support manager module allows the user to create their custom set of "user pre-defined hierarchy of referenced material." The names of this material, may be defined by the user in their native language, obviating the need for a translation. The user may attach a pre-prepared file (text and graphics) to the name created by the user for a reference material in a format chosen by the user. The user may have the ability to link this material to an already defined protocol task provided by the protocol assistant module or a smart message provided by the smart messaging module to allow the user easier access during use.

Figure 19:
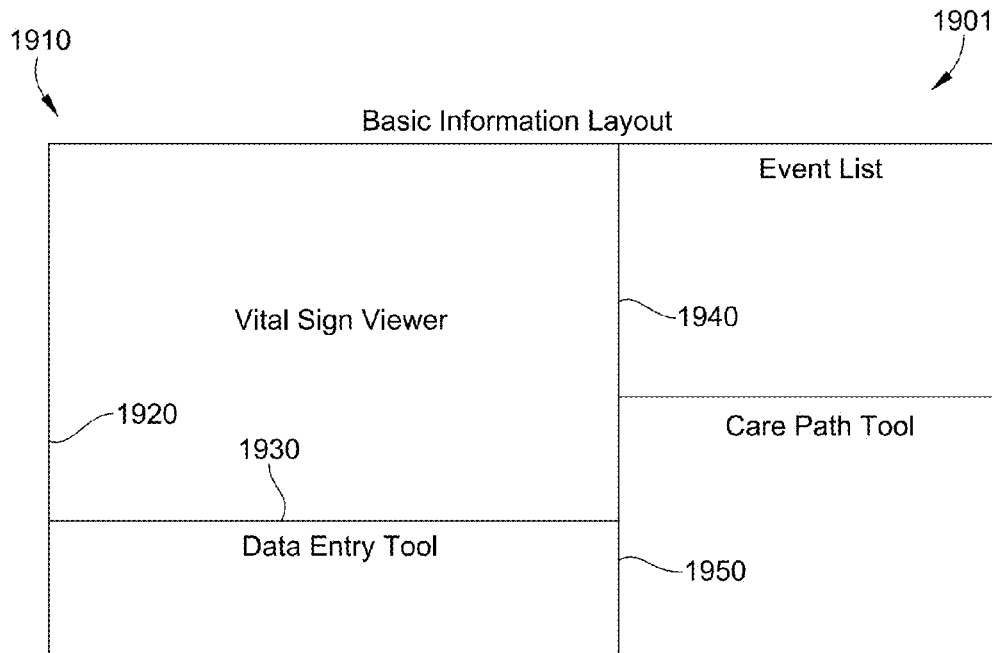
FIGS. 19-21 show an architecture and display generated by the dashboard generator shown in FIG. 4.
Figure 20:
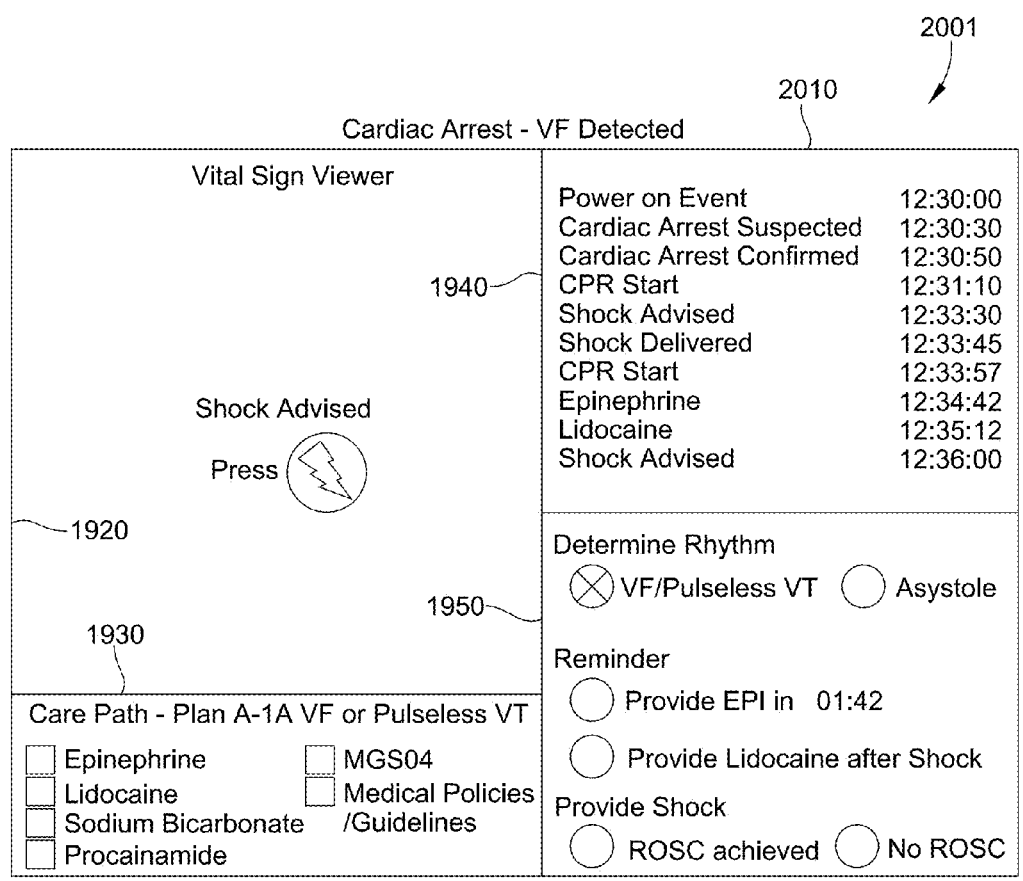
Figure 21:
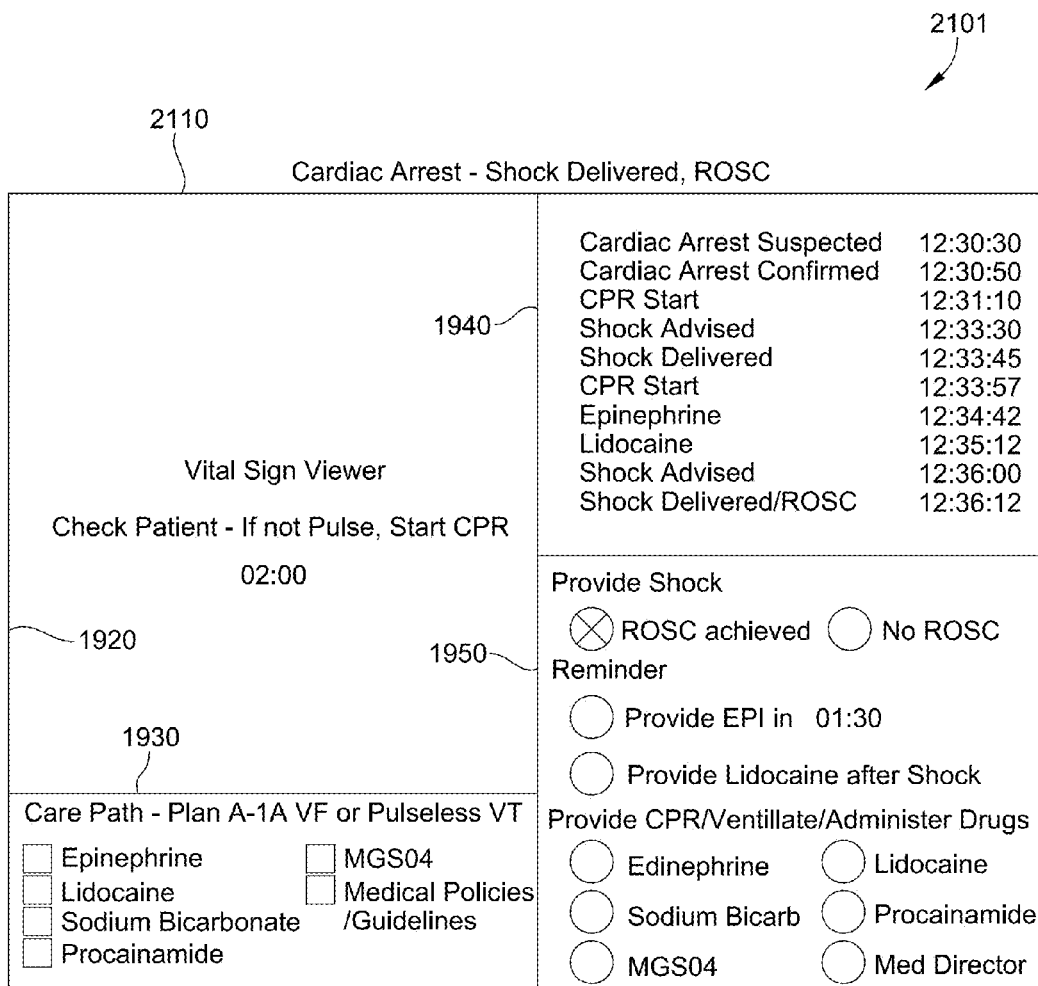

As previously described in FIG. 4, the dashboard generator 494 is hardware and software configured to provide a display of the dependency graphs of the various workflow tasks of the work flow of interdependent tasks defined by the task file module 470 using task configurations for each task provided by the configuration files module 480. FIGS. 19-21 show an illustrative architecture and display generated by the dashboard generator 494 shown in FIG. 4. More particularly, FIG. 19 shows a defibrillator 1910 of a defibrillator system 1901 displaying illustrative screen shot 1920 illustrating a partitioning of the display into a vital sign viewer 1920, a data entry tool 1930, an event list 1940, and a care path tool 1950. The vital sign viewer may illustratively display vital signs of a patient such as a spark line. FIG. 20 shows the vital sign viewer 1920 which displays an instruction from the protocol assistant module advising to apply a shock and displays an active button for the caregiver to press to apply an electrical shock from the defibrillator to the patient. The data entry tool 1930 includes a checklist of tasks for an illustrative care path that a user may take. The tasks generated by the protocol assistant module are for the cardiac arrest protocol previously selected by the user. The event list 1940 includes a listing of events generated by the event viewer module that have occurred during the cardiac arrest protocol each shown stamped with the time at which the event occurred. The care path tool 1950 includes an illustrative checklist of tasks generated by the protocol assistant module for the cardiac arrest protocol previously selected by the user. The care path tool shows that the VF/Pulseless VT condition has been checked by the user which navigates the protocol through appropriate follow-on screen shots of tasks applicable to the VF/Pulseless VT condition. The care path tool also provides a reminder generated by the smart messaging module reminding the user to provide EPIn on the 01:42 hour. The care path tool also provides a follow-on task to determine whether a return of spontaneous circulation (RPSC) has been achieved after application of a shock.

The display shown in FIG. 21 has been advanced to a later point in time than shown in the display shown in FIG. 20. In particular, FIG. 21 shows in the event list 1940 that the user delivered the shock recommended in vital sign viewer 1920 of FIG. 20 at the hour of 12:36.12. As FIG. 21 shows, at this point in the process the vital sign viewer 1920 is now displaying the next task in the protocol generated by the protocol assistant module which is "Check Patient—Of not Pulse, Start CPR" and indicating a 02:00 minute window to start CPR. The user may then refer to the vital sign viewer 1920, the data entry tool 1930, the event list 1940, and the care path tool 1950 to make the next set of informed decisions that a caregiver is being required to make in the treatment of this patient.

Figure 22A:
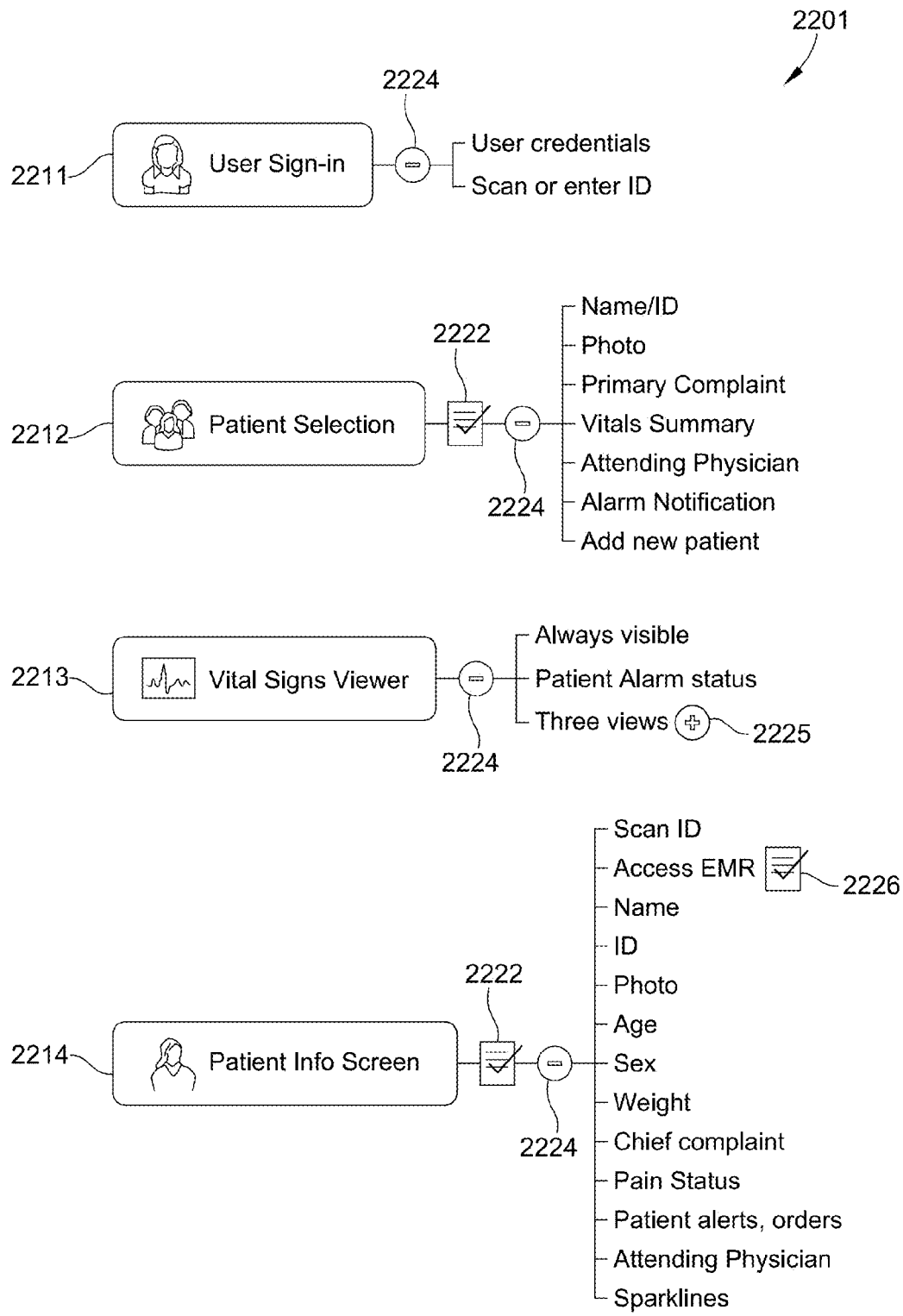
FIGS. 22A, B show an illustrative flow for configuring a decision support module in accordance with this disclosure.
Figure 22B:
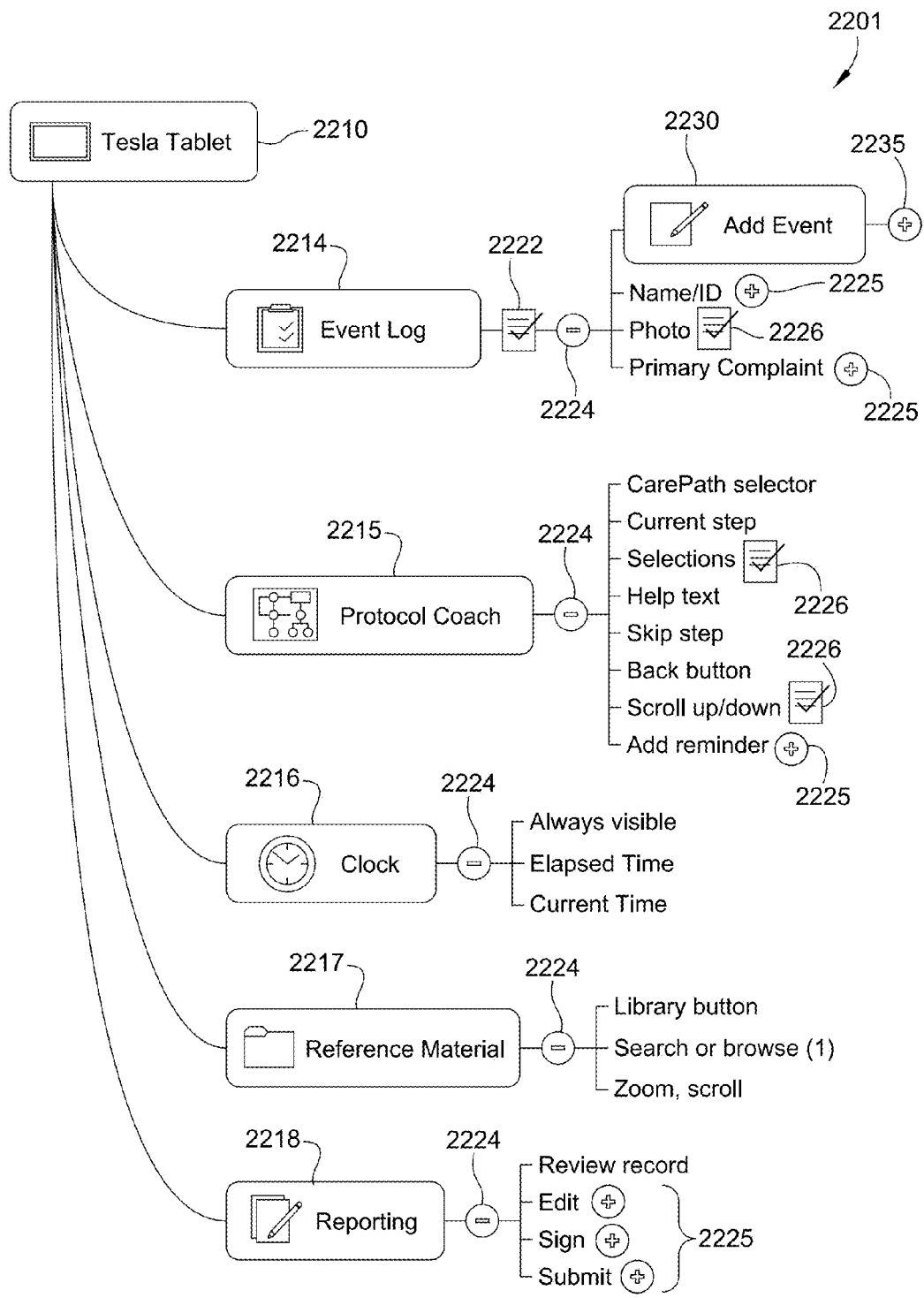

FIGS. 22A and 22B show an illustratively menu 2201 illustrating one manner ways in which the events, protocols, messages, smart indices, and reference material lookups of this disclosure may be further customized by the workflow creation module 701 of FIG. 7 for the creation of a workflow according to this disclosure. The illustrated workflow is being created by the workflow creator on a tablet 2210 in this example. The menu 2201 includes one or more entries for user sign unit 2211, a patient selection unit 2212, a vital signs viewer unit 2213, a patient info screen unit 2214, an event log unit 2214, a protocol coach unit 2215, a clock 2216, a reference material unit 2217, and a reporting unit 2218. Each unit includes an illustrative set of actions that a user may take once in a unit to configure the units to enable a decision support module of this disclosure to be further customized to a user. As previously described in FIGS. 8 and 9, this workflow may be distributed and downloaded to individual defibrillators; thereby enabling users navigate through the decision support module according to the navigational map illustrated in FIGS. 22A, B or other navigational maps that may be downloaded. As FIGS. 22A, B further illustrate, certain of the nodes on the navigational map are expandable and/or may be selected or deselected using check-marks 2212, 2214, 2225, and 2226.

In alternative embodiments, the vital sign viewer and general purpose data areas of a display may grow or shrink as requested/necessary. Both areas may have information that is required, and optional. Typically, the required information may be shown when shrunk. A keyboard may be shown at the bottom of the general purpose data Area when a data entry field is selected; thereby enabling touch screen entry of data for configuring the data support module. Typically, the display may always display a clock. The current time may be shown at the top of the general purpose area. An elapsed time may be shown in the event list. A vital sign viewer may be displayed for all modes, typically except for patient selection, and reporting. The user may configure which general purpose area selection they want to start in. The defibrillator may be provided with a wireless bar code reader to read patient name, ID, and alerts from bracelet review/edit. Final report types may be based on the protocols selected (Code/RRT, others). Pop-ups may be used by some general purpose modes if some type of alarm, alert, overdue reminder, etc. is detected and would be masked in the current view.

The vital sign viewer may be maximized or minimized, the vital sign values may be provided with alarm indicators, A regions of the display may display an alert. The general purpose data area of the patient selector may display multiple patients, provide top level status of patient, vital signs, alerts, alarms, allow for addition or removal of patients, allow selection of a particular patient and opening up of a patient status/trends report, enable pop-ups during the other modes, such as if a patient alarm, alert, or reminder goes off. Patient information and demographics may allow a user to enter patient information or capture form EMR such as name, ID, age, sex, weight, chief complaint, pain status, patient alerts (e.g., allergies, previous codes, DNR orders, etc.), medical authority, such as who has patient's treatment approval rights. Patient status/trends data may include an event list which could have the same capability wherever it is called out, elapsed time clock, such as at the top of the display, running list of events, scrollable, up and down, ability to select event and pop up event summary, simplified version of waveform event in code summary.

Patient trends may include a sparkline view of some or all vital signs collected since power on, patient summary information (such as manually entered by the User). Free form data entry of events may include event list, adding event button, event selection hierarchy, data entry forms (if applicable for selected event. Protocol selections/protocols may include a protocol selection hierarchy (with button to bring up). Current protocol step may include name of activity, help text, activity selections, reminder section, automatic reminders from protocols, with ability to select/reject, button to create a manual reminder, reminder name, time period to reminder, repeat yes/no. General reference material may include button to bring up reference material selector, ability to select for a list or set of icons, view selected .pdf material, allow zoom in, or out, page up.down. Patient EMR data may include ability to select to view current patient status information from electronic medical record, view selected patients report (.pdf material). It may also include admittance date, admittance complaint, treatment orders/results, current diagnosis/treatment narrative, patient record review and save, ability to review final report (Code or RRT), ability to edit any fields, add, delete events, change text values, capture digital signature for report, save report to the system (LIFENET and EMRs).

There is thus disclosed a module, a system and a method for modeling work flows as a graph of interdependent tasks to be performed. The tasks to be performed are set by a task file module configured to enable interactions between tasks and including modules for event viewing, protocol assistance, smart messaging, smart indices, reference material lookup. A decision support manager module is configured to construct data and model profiles for storage in a data and model profile bank, events for storage in a decision support events bank, and protocols for storage in a decision support protocol bank. Configuration files are provided to specify a configuration for execution of one of the tasks. Data entered through a user interface or from a network via a wireless or wired communication module may define task files in the task files module, configuration files in the configuration files module, as well as data, events, and protocols to be used for a defibrillation procedure. A decision support manager module is configured to construct a dependency graph of tasks as specified in at least one of the configuration files and to execute the dependency graph.

A workflow creation module of this disclosure serves as an editor advantageously for the creation of the workflow for the medical devices, such as defibrillators. In other words, the workflow creation module may provide the editor for configuring the configuration of the decision support module of the medical device; illustratively providing configurations for the configuration files in the configuration file module of the decision support module on the medical device. For example, the workflow creation module may define the protocols that the decision support module is to follow in managing the clinical display on the medical device. The workflow creation module may further configure clinical data residing on servers that may be accessed by the medical device with protocols, rules, etc. for delivery and display to the decision support module according to this disclosure.

The module, system, and method of this disclosure helps avoid missed steps that can lead to errors by helping users to follow steps of a checklist, algorithm, mnemonic, protocol, guideline, etc. The disclosure helps align a caregiver and supporting team on the current or upcoming activity and the time critical elements of the intervention. The disclosure facilitates real-time documentation during emergencies, with simpler interfaces, prompted selection and automated time stamping. The disclosure enables QA review of how well the team responded or managed the emergency, in relation to the information used above. These and other advantages are made possible by this disclosure.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. For use in a medical device for providing decision support to a caregiver:
   a defibrillation processor configured to control an administration of an electrical charge as part of a defibrillation administration; and
   a decision support module configured to provide decision support to the caregiver during operation of the medical device, the decision support module comprising:
   a task file module configured to manage one or more task files, the task files defining a workflow of one or more interdependent tasks to be performed and defining and enabling interactions between the interdependent tasks;
   a configuration file module configured to manage one or more configuration files, the configuration files specifying a configuration for execution of the one or more interdependent tasks by providing configurations for data and data flows for a task defined by the task files of the task file module;

a bank configured to provide one or more of: data, model profiles, events, and protocols to the decision support module, the bank fed with medical data from the medical device;

a decision support manager module configured to construct a dependency graph modeling the workflow of interdependent tasks defined by the task files of the task file module using configurations for each interdependent task provided by the configuration file module; and a dashboard generator configured to provide a visual, audio, or audio-visual display, based on the dependency graph constructed by the decision support manager module, the visual, audio, or audio-visual display configured to provide enhanced coaching to the caregiver to cause the caregiver to perform at least one of a treatment or monitoring, at least one of the treatment including administration of a treatment via the defibrillation processor.

2. The decision support module of claim 1 wherein the medical device is configured to be operated to deliver a defibrillator pulse.

3. The decision support module of claim 1 wherein the task file module includes one or more modules selected from the group consisting of:
an event viewer module;
a protocol
assistant module;
a smart
messaging
module; a smart
indices module;
and
a reference material lookup module.

4. The decision support module of claim 1 further comprising an event viewer module configured to generate a series of time stamped events for tracking events that happened with a patient.

5. The decision support module of claim 1 further comprising a dashboard generator module and an event viewer module;
wherein the dashboard generator module is configured to generate a non-indexed view of a major vital sign as it varies over time; and
wherein the event viewer module is configured to provide an event marker at a point in time along the non-indexed view of the major vital sign, the event marker providing a record of one or more predetermined events associated with the major vital sign at that point in time.

6. The decision support module of claim 5 wherein the one or more predetermined events provided in the record of the event marker is taken from the group of predetermined events consisting of an indexed view of the major vital sign, a view of the major vital sign over a specific period of time, a specific event, details of a specific event, a time stamped event, a listing of time stamped events, a view of one or more different vital signs at that point in time, and a combination of one or more predetermined events thereof.

7. The decision support module of claim 5 wherein the record of the event marker is configurable by a user with one or more new events.

8. The decision support module of claim 7 further comprising a predetermined hierarchy of manually programmable events, the hierarchy of manually programmable events providing the one or more new events selectable by the user configuring the record of the event marker.

9. The decision support module of claim 5 wherein the record of the event marker is provided with a link back to the event marker, the link back enabling a user to return to the major vital sign as it varies over time.

10. The decision support module of claim 5 wherein the major vital sign is one of a group consisting of heart beat, $SpO_2$, $CO_2$, temperature, an oxygen saturation in the blood of a patient; a chest compression of a patient; an image of the internal structure of a patient; an oxygen saturation in the blood in the brain of a patient; the acidity or alkalinity of fluids in a patient; and other patient parameter.

11. The decision support module of claim 1 further comprising an event viewer module configured to associate an event marker to an event, the event marker providing a record of one or more predetermined events associated with the event.

12. The decision support module of claim 1 further comprising an event viewer module configured to generate a series of time stamped events for tracking a condition of a patient.

13. The decision support module of claim 12 wherein the series of time stamped events is contained in a record.

14. The decision support module of claim 1 further comprising a protocol assistant module configured to generate a protocol of one or more activities.

15. The decision support module of claim 1 further comprising a dashboard generator configured to generate a display of one or more activities and a checklist of tasks for a care path.

16. The decision support module of claim 14 wherein the protocol assistant module is further configured to generate a time stamp for each activity of the protocol when completed.

17. The decision support module of claim 14 wherein the one or more of the activities is associated with an event that is automatically generated at the time the activity of the protocol is completed.

18. The decision support module of claim 14 wherein the one or more activities of the protocol are displayed in a primary work area of a display, and wherein information that was displayed in the primary work area of the display is moved to a background of the display.

19. The decision support module of claim 14 wherein the one or more activities of the protocol are displayed in a primary work area of a display unless clinically critical information is displayed in the primary work area of the display at the time the protocol is to be displayed.

20. The decision support module of claim 14 wherein the protocol assistant module is configured to access a Sparkline non-indexed view of a major vital sign as it varies over time and to access an event marker at a point in time along the non-indexed view of the major vital sign generated by an event viewer module and to access a record of one or more predetermined events associated with the major vital sign at that point in time provided by the event marker.

21. The decision support module of claim 14 wherein the protocol assistant module is further configured to automatically appear on a display when one or more pre- determined events occur.

22. The decision support module of claim 14 wherein the protocol assistant module is manually selectable using a protocol key.

23. The decision support module of claim 14 further comprising a user defined hierarchy of one or more protocols selectable by the user to configure the protocol generated by the decision support module.

24. The decision support module of claim 14 further comprising a system defined hierarchy of one or more protocols selectable by a user to configure the protocol generated by the decision support module.

25. The decision support module of claim 1 further comprising a smart messaging module configured to generate a set of one or more predefined messages to inform a user of an action.

26. The decision support module of claim 25 wherein the action informed by the one or more predefined messages is taken from a group of actions consisting of a reminder, a reminder to take a medication, and a suggestion to contact one or more persons.

27. The decision support module of claim 25 wherein the set of predefined messages appears as a pop-up on a display.

28. The decision support module of claim 27 wherein the pop-up is displayed in a general work area of the display.

29. The decision support module of claim 28 wherein the general work area is a bottom waveform region.

30. The decision support module of claim 25, wherein the smart messaging module is further configured to receive, from a user, an acknowledgement or cancellation of one or more of the predefined messages and wherein a record is made of the acknowledgement or cancellation.

31. The decision support module of claim 30 wherein the acknowledgement is associated with an event that is automatically generated at the time of the acknowledgement.

32. The decision support module of claim 25 wherein the smart messaging module is further configured to generate the set of one or more predefined messages on the occurrence of an initiating event or a time based Boolean Equation using a combination of vital sign data and events.

33. The decision support module of claim 25 wherein the predefined message is configured to generate an output response that is selected from a group consisting of no output response, an output response tied to a standard set of events, and an output response based on a user predefined hierarchy of manually enterable events.

34. The decision support module of claim 1 further comprising a smart indices module configured to generate a predefined indice value associated with an overall patient condition.

35. The decision support module of claim 34 wherein the smart indices module is further configured to generate the predefined indice value by a predefined indices algorithm.

36. The decision support module of claim 34 wherein the indice value appears as a vital sign information on a display.

37. The decision support module of claim 34 wherein the indice value will appear throughout a patient episode.

38. The decision support module of claim 34 wherein the indice value can be programmed to appear at the beginning of a patient episode, manually selectable via a indices menu, or automatically displayed by initiating an event.

39. The decision support module of claim 1 further comprising a reference material lookup module configured to display either a user defined set of text or graphical information in a predetermined content format.

40. The decision support module of claim 39 wherein the predetermined content format is selected from a group of formats consisting of .pdf, .doc, and html5.

41. The decision support module of claim 39 wherein the user defined set of text or graphical information is accessed manually via a user defined hierarchical menu of reference material.

42. The decision support module of claim 39 wherein the user defined set of text or graphical information is generated when the reference material is associated with a protocol task of a smart message.

43. The decision support module of claim 39 wherein preprogrammed information is displayed in a general work area of a display.

44. The decision support module of claim 43 wherein the general work area is in a bottom region of the display.

45. The decision support module of claim 43 further configured to provide a menu to enable a user to scroll through the preprogrammed information.

46. A system for providing decision support to a caregiver comprising:
  a medical device comprising:
    a treatment module configured to at least one of administer a treatment, control administration of a treatment or assist an administration of a treatment, the treatment including delivery of a defibrillation pulse;
    a decision support module comprising:
      a task file configured to define a workflow of one or more interdependent tasks to be performed and to define and enable interactions between the interdependent task;
      a configuration file configured to specify a configuration for execution of the one or more interdependent tasks by providing configurations for data and data flows for a task defined by the task files of a task file module;
      a data and model profile bank configured to store one or more of data and one or more model profiles for the task file;
      a decision support event bank configured to store one or more events for the task file;
      a decision support protocol bank configured to store one or more priorities for the task file; and
      a decision support manager module configured to construct a dependency graph of tasks as specified in the configuration file, the dependency graph providing enhanced coaching to the caregiver to cause the caregiver to perform at least one of a treatment or monitoring, the treatment including at least one of treatment via the treatment module or treatment assisted by the treatment module; and
  an external utility in communication with the medical device configured to exchange data between the medical device and the external utility for one or more of configuring the task file, configuring the configuration file, feeding data and model profile to the data and model profile bank, feeding decision support events to the decision support event bank, and feeding decision support protocols to the decision protocol bank.

47. The system of claim 46 wherein the medical device comprises a defibrillator operable to deliver the defibrillation pulse.

48. The system of claim 47 wherein the defibrillator includes a module selected from the group consisting of:
  an event viewer module;
  a protocol assistant module;
  a smart messaging module;
  a smart indices module; and
  a reference material lookup module.

49. The system of claim 47, wherein the system is configured to communicate the dependency graph using a display of the defibrillator.

50. The system of claim 47 wherein the system is configured to communicate the dependency graph in audio format over a loud speaker of the defibrillator.

51. The system of claim 46 further comprising:
  a user interface for entering data into the medical device for one or more of: configuring the task file, configuring the configuration file, feeding data and model profile to the data and model profile bank, feeding decision support events to the decision support event bank, and feeding decision support protocols to the decision protocol bank.

52. The system of claim 46 wherein the external utility is selected from a group consisting of a medical monitor, a commercial tablet, a personal computer, and a smartphone.

* * * * *

UNITED STATES PATENT AND TRADEMARK OFFICE
CERTIFICATE OF CORRECTION

PATENT NO. : 10,303,852 B2
APPLICATION NO. : 13/836769
DATED : May 28, 2019
INVENTOR(S) : Ken Peterson et al.

Page 1 of 1

It is certified that error appears in the above-identified patent and that said Letters Patent is hereby corrected as shown below:

Application Data, (71) Applicant should read: -- Physio-Control, Inc. --

Signed and Sealed this
Tenth Day of December, 2019

Andrei Iancu
*Director of the United States Patent and Trademark Office*